(12) United States Patent
Lippa et al.

(10) Patent No.: US 9,393,204 B2
(45) Date of Patent: Jul. 19, 2016

(54) METHODS AND COMPOSITIONS EMPLOYING BICIFADINE FOR TREATING DISABILITY OR FUNCTIONAL IMPAIRMENT ASSOCIATED WITH ACUTE PAIN, CHRONIC PAIN, OR NEUROPATHIC DISORDERS

(71) Applicant: EBI Life Sciences, Inc., Cambridge, MA (US)

(72) Inventors: Arnold S. Lippa, Ridgewood, NJ (US); Warren Stern, Plymouth, MA (US); Johnson Lim, Edison, NJ (US)

(73) Assignee: EBI Life Sciences, Inc., Cambridge, MA (US)

( * ) Notice: Subject to any disclaimer, the term of this patent is extended or adjusted under 35 U.S.C. 154(b) by 0 days.

(21) Appl. No.: 13/907,920

(22) Filed: Jun. 2, 2013

(65) Prior Publication Data
US 2013/0345280 A1    Dec. 26, 2013

Related U.S. Application Data

(63) Continuation of application No. 13/742,335, filed on Jan. 15, 2013, now abandoned, which is a continuation of application No. 13/488,341, filed on Jun. 4, 2012, now abandoned, which is a continuation of application No. 13/297,439, filed on Nov. 16, 2011, now abandoned, which is a continuation of application No. 11/708,951, filed on Feb. 20, 2007, now abandoned, which is a continuation of application No. 11/438,909, filed on May 22, 2006, now abandoned, which is a continuation-in-part of application No. 11/260,887, filed on Oct. 26, 2005, now abandoned, which is a continuation-in-part of application No. 10/621,435, filed on Jul. 17, 2003, now abandoned.

(60) Provisional application No. 60/399,852, filed on Jul. 31, 2002.

(51) Int. Cl.
*A61K 31/403* (2006.01)
*A61K 9/20* (2006.01)

(52) U.S. Cl.
CPC ............ *A61K 9/2054* (2013.01); *A61K 31/403* (2013.01)

(58) Field of Classification Search
CPC ........................................................ A61K 31/41
USPC ........................................................ 514/410
See application file for complete search history.

(56) References Cited

U.S. PATENT DOCUMENTS

| | | | |
|---|---|---|---|
| 3,892,722 A | 7/1975 | Babitsky et al. | |
| 4,022,652 A | 5/1977 | Hirano et al. | |
| 4,088,652 A | 5/1978 | Fanshawe et al. | |
| 4,118,393 A | 10/1978 | Fanshawe et al. | |
| 4,118,417 A | 10/1978 | Epstein | |
| 4,131,611 A | 12/1978 | Fanshawe et al. | |
| 4,196,120 A | 4/1980 | Fanshawe et al. | |
| 4,231,935 A * | 11/1980 | Fanshawe et al. | ............ 548/515 |
| 4,336,268 A | 6/1982 | Bruderer et al. | |
| 4,435,419 A | 3/1984 | Epstein et al. | |
| 4,504,657 A | 3/1985 | Bouzard et al. | |
| 4,521,431 A | 6/1985 | Crookes | |
| 4,591,598 A | 5/1986 | Urbach et al. | |
| 5,039,680 A | 8/1991 | Imperato et al. | |
| 5,075,341 A | 12/1991 | Mendelson et al. | |
| 5,130,430 A | 7/1992 | Shaw | |
| 5,198,459 A | 3/1993 | Imperato et al. | |
| 5,232,934 A | 8/1993 | Downs | |
| 5,488,056 A | 1/1996 | Bodick et al. | |
| 5,556,837 A | 9/1996 | Nestler et al. | |
| 5,556,838 A | 9/1996 | Mayer et al. | |
| 5,574,052 A | 11/1996 | Rose et al. | |
| 5,762,925 A | 6/1998 | Sagen | |
| 5,911,992 A | 6/1999 | Braswell et al. | |
| 5,969,156 A | 10/1999 | Briggs et al. | |
| 5,985,864 A | 11/1999 | Imai et al. | |
| 6,109,269 A | 8/2000 | Rise et al. | |
| 6,121,261 A | 9/2000 | Glatt et al. | |
| 6,194,000 B1 | 2/2001 | Smith et al. | |
| 6,204,284 B1 | 3/2001 | Beer et al. | |
| 6,245,911 B1 | 6/2001 | Imai et al. | |
| 6,372,919 B1 | 4/2002 | Lippa et al. | |
| 6,569,887 B2 | 5/2003 | Lippa et al. | |
| 6,716,868 B2 | 4/2004 | Lippa et al. | |
| 7,041,835 B2 | 5/2006 | Lippa et al. | |
| 7,081,471 B2 | 7/2006 | Lippa et al. | |
| 7,094,799 B2 | 8/2006 | Russell et al. | |
| 7,098,229 B2 | 8/2006 | Lippa et al. | |
| 7,098,230 B2 | 8/2006 | Lippa et al. | |
| 2004/0058896 A1 | 3/2004 | Dietrich et al. | |
| 2004/0102638 A1 | 5/2004 | Russell et al. | |

(Continued)

FOREIGN PATENT DOCUMENTS

| | | |
|---|---|---|
| AU | 519620 B2 | 12/1981 |
| BE | 858683 | 3/1978 |
| BE | 893707 | 12/1982 |

OTHER PUBLICATIONS

U.S. Appl. No. 10/466,457, filed Feb. 10, 2004, Lippa et al.
U.S. Appl. No. 10/702,397, filed Nov. 5, 2003, Russell et al.
U.S. Appl. No. 10/764,371, filed Jan. 23, 2004, Lippa et al.
U.S. Appl. No. 10/764,373, filed Jan. 23, 2004, Lippa et al.
U.S. Appl. No. 10/764,375, filed Jan. 23, 2004, Lippa et al.
U.S. Appl. No. 11/205,956, filed Aug. 16, 2005, Hagen et al.
U.S. Appl. No. 11/254,242, filed Oct. 18, 2005, Lippa et al.
U.S. Appl. No. 11/263,045, filed Oct. 31, 2005, Basile et al.
U.S. Appl. No. 11/371,178, filed Mar. 7, 2006, Skolnick et al.
Baldessarini, R., "Drugs and the Treatment of Psychiatric Disorders" in Goodman and Gilman's The Pharmacological Basis of Therapeutics, Ninth Edition, J. Hardman et al., Eds., McGraw-Hill, New York, 1996, p. 399 and Chapter 18, pp. 431-459.
Bayes, M. et al., "Gateways to Clinical Trials," Methods and Findings in Experimental and Clinical Pharmacology, 2003, 25 (3), 225-248.

(Continued)

*Primary Examiner* — Raymond Henley, III
(74) *Attorney, Agent, or Firm* — Hoxie & Associates LLC

(57) ABSTRACT

Methods and compositions are provided for formulating and administering bicifadine and related compounds to treat or prevent functional impairment and disabilities associated with acute pain, chronic pain, and neuropathic disorders.

28 Claims, 3 Drawing Sheets

(56) References Cited

U.S. PATENT DOCUMENTS

| | | |
|---|---|---|
| 2004/0127541 A1 | 7/2004 | Codd et al. |
| 2004/0132797 A1 | 7/2004 | Lippa et al. |
| 2004/0157869 A1 | 8/2004 | Lippa et al. |
| 2004/0157870 A1 | 8/2004 | Lippa et al. |
| 2004/0157908 A1 | 8/2004 | Lippa et al. |
| 2006/0019966 A1 | 1/2006 | Deecher et al. |
| 2006/0020014 A1 | 1/2006 | Abou-Gharbia et al. |
| 2006/0020015 A1 | 1/2006 | Abou-Gharbia et al. |
| 2006/0100263 A1 | 5/2006 | Basile et al. |
| 2006/0173064 A1 | 8/2006 | Lippa et al. |
| 2006/0223875 A1 | 10/2006 | Skolnick et al. |
| 2007/0021488 A1 | 1/2007 | Abou-Gharbia |
| 2007/0043100 A1 | 2/2007 | Hagen et al. |
| 2007/0082938 A1 | 4/2007 | Russell et al. |
| 2008/0009538 A1 | 1/2008 | Skolnick |
| 2008/0014272 A1 | 1/2008 | Skolnick et al. |

OTHER PUBLICATIONS

Beer, B. et al., "DOV 216,303, A 'Triple' Reuptake Inhibitor: Safety, Tolerability, and Pharmacokinetic Profile," The Journal of Clinical Pharmacology, 2004, 44 (12), 1360-1367.

Blum, K. et al., "Dopamine D2 Receptor Gene Variants: Association and Linkage Studies in Impulsive-Addictive-Compulsive Behaviour," Pharmacogenetics, 1995, 5 (3), 121-141.

Bray, G., "A Concise Review on the Therapeutics of Obesity," Nutrition, 2000, 16 (10), 953-960.

U.S. Appl. No. 11/384,219, filed Mar. 17, 2006, Skolnick.

U.S. Appl. No. 11/433,790, filed May 12, 2006, Russell et al.

U.S. Appl. No. 11/445,950, filed Jun. 2, 2006, Russell et al.

U.S. Appl. No. 60/702,800, filed Jul. 26, 2005, Lippa et al.

U.S. Appl. No. 60/703,364, filed Jul. 27, 2005, Skolnick et al.

Crown, W., "Economic Outcomes Associated with Tricyclic Antidepressant and Selective Serotonin Reuptake Inhibitor Treatments for Depression," Acta Psychiatrica Scandinavica Supplementum, 2000, 403, 62-66.

Czobor, P., "A Double-Blind, Placebo Controlled Randomized Study of DOV 220,075 (Bicifadine) SR and Codeine 60 mg in the Treatment of Post-Operative Dental Pain," American Pain Society 2003, Abstract (915).

Czobor, P., "A Two Center Double-Blind Placebo-Controlled Randomized Study of DOV 220,075 (Bicifadine) SR and Tramadol 100 mg in the Treatment of Post-Operative Dental Pain," American Pain Society, 2004, Abstract (801).

D'Aquila, P. et al., "The Role of Dopamine in the Mechanism of Action of Antidepressant Drugs," European Journal of Pharmacology, 2000, 405 (1-3), 365-373.

Derwent Abstract for BE 858,683, 3 pages.

Derwent Abstract for BE 893,707, 2 pages.

Epstein, J. et al., "1-Aryl-3-azabicyclo[3.1.0]hexanes, A New Series of Nonnarcotic Analgesic Agents," Journal of Medicinal Chemistry, 1981, 24 (5), 481-490.

Epstein, J. et al., "Bicifadine: Non-Narcotic Analgesic Activity of 1-Aryl-3-Azabicycl[3.1.0]Hexanes," NIDA Research Monograph, 1982, 41, 93-98.

Fauci, A. et al., Eds., Harrison's Principles of Internal Medicine, Fourteenth Edition, 1998, pp. 2485-2503.

Frazer, A. "Norepinephrine Involvement in Antidepressant Action," Journal of Clinical Psychiatry, 2000, 61 (Suppl. 10), 25-30.

Fredman, S. et al., "Partial Response, Nonresponse, and Relapse with Selective Serotonin Reuptake Inhibitors in Major Depression: A Survey of Current 'Next-Step' Practices," Journal of Clinical Psychiatry, 2000, 61 (6), 403-408.

Grant, J., Ed., Hackh's Chemical Dictionary, Fourth Edition, McGraw-Hill Book Company, New York, 1969, pp. 474-475.

Hitri, A. et al., "Molecular, Functional and Biochemical Characteristics of the Dopamine Transporter: Regional Differences and Clinical Relevance," Clinical Neuropharmacology, 1994, 17 (1), 1-22.

Hoffman, B. et al., "Localization and Dynamic Regulation of Biogenic Amine Transporters in the Mammalian Central Nervous System," Frontiers in Neuroendocrinology, 1998, 19 (3), 187-231.

Kiyatkin, E., "Dopamine Mechanisms of Cocaine Addiction," The International Journal of Neuroscience, 1994, 78 (1-2), 75-101.

Kreek, M., "Cocaine, Dopamine and the Endogenous Opiod System," Journal of Addictive Diseases, 1996, 15 (14), 73-96.

Leonhardt, M. et al., "New Approaches in the Pharmacological Treatment of Obesity," European Journal of Nutrition, 1999, 38 (1), 1-13.

Mcardle, P. et al., "A Method for the Prediction of the Crystal Structure of Ionic Organic Compounds—The Crystal Structures of O-Toluidinium Chloride and Bromide and Polymorphism of Bicifadine Hydrochloride," CrystEngComm, 2004, 6 (53), 303-309.

Meyerson, L. et al., "Allosteric Interaction Between the Site Labeled by [$^3$H]Imipramine and the Serotonin Transporter in Human Platelets," Journal of Neurochemistry, 1987, 48 (2), 560-565.

Nagatsu, T. et al., "Changes in Cytokines and Neurotrophins in Parkinson's Disease," Journal of Neural Transmission. Supplementa, 2000, 60, 277-290.

Noble, E., "Polymorphisms of the D2 Dopamine Receptor Gene and Alcoholism and Other Substance Use Disorders," Alcohol and Alcoholism—Supplements, 1994, 2, 35-43.

Porter, E., "Single Dose Comparison of Bicifadine, Codeine, and Placebo in Postoperative Pain," Current Therapeutic Research, 1981, 30 (3), 156-160.

Scates, A. et al., "Reboxetine: A Selective Norepinephrine Reuptake Inhibitor for the Treatment of Depression," The Annals of Pharmacotherapy, 2000, 34 (11), 1302-1312.

Simon, G. et al., "TCAs or SSRIs As Initial Therapy for Depression," Journal of Family Practice, 1999, 48, 845-846.

Skolnick, P., "Beyond Monoamine-Based Therapies: Clues to New Approaches," Journal of Clinical Psychiatry, 2002, 63 (Suppl. 2), 19-23.

Skolnick, P. et al., "Antidepressant-like Actions of DOV 21,947, A 'Triple' Uptake Inhibitor," European Journal of Pharmacology, 2003, 461, 99-104.

Skolnick, P. et al., "'Broad Spectrum' Antidepressants: Is More Better for the Treatment of Depression," Life Sciences, 2003, 73 (25), 3175-3179.

Stacy, M. et al., "Treatment Options for Early Parkinson's Disease," American Family Physician, 1996, 53 (4), 1281-1287.

Sullivan, A. et al., "Mechanisms of Appetite Modulation by Drugs," Federation Proceedings, 1985, 44 (1 Pt. 1), 139-144.

Wang, R. et al., "The Oral Analgesic Efficacy of Bicifadine Hydrochloride in Postoperative Pain," The Journal of Clinical Pharmacology, 1982, 22 (4), 160-164.

Wong, E. et al., "Reboxetine: A Pharmacologically Potent, Selective, and Specific Norepinephrine Reuptake Inhibitor," Biological Psychiatry, 2000, 47 (9), 818-829.

U.S. Appl. No. 11/260,887, filed Oct. 26, 205, Lippa et al.

U.S. Appl. No. 11/438,909, filed May 22, 2006, Lippa et al.

Brittain, H., Ed., "Effects of Pharmaceutical Processing on Drug Polymorphs and Solvates" in Polymorphism in Pharmaceutical Solids, 1999, 95, 348-361.

Cheronis, N., Semimicro Experimental Organic Chemistry, 1958, Chapter 5, 31-49.

Miller, L. et al., "Preparative Chromatographic Resolution of Enantiomers Using Polar Organic Solvents with Polysaccharide Chiral Stationary Phases," Journal of Chromatography A, 1999, 865, 211-226.

* cited by examiner

Bicifadine IR vs SR

Mean plasma concentration time course data on Day 4 following administration of 200mg BID, 200mg TID, and 400mg BID (multiple dose, steady-state profiles within a dosing interval at steady state)

Acute Dental Pain
Summed Pain Relief and Intensity Difference Up to 6 Hours

Efficacy: VAS Pain Scores

RDQ Responder Analysis (50% improvement) for RDQ > 17 Baseline

Pain Responder Analysis for RDQ > 17 at Baseline
Responders = Patients Showing At Least a 50% Improvement in VAS Pain Score

METHODS AND COMPOSITIONS EMPLOYING BICIFADINE FOR TREATING DISABILITY OR FUNCTIONAL IMPAIRMENT ASSOCIATED WITH ACUTE PAIN, CHRONIC PAIN, OR NEUROPATHIC DISORDERS

CROSS-REFERENCE TO RELATED APPLICATIONS

This application claims priority as a CONTINUATION of prior application U.S. patent application Ser. No. 13/742,335, filed Jan. 15, 2013, now abandoned, which is a continuation of U.S. patent application Ser. No. 13/488,341, filed Jun. 4, 2012, now abandoned, which is a continuation of U.S. patent application Ser. No. 13/297,439, filed Nov. 16, 2011, now abandoned, which is a continuation of U.S. patent application Ser. No. 11/708,951, filed Feb. 20, 2007, now abandoned, which is a continuation of U.S. patent application Ser. No. 11/438,909, filed May 22, 2006, now abandoned, which is a continuation-in-part of U.S. patent application Ser. No. 11/260,887, filed Oct. 26, 2005, now abandoned, the disclosure of each for which priority is claimed and incorporated herein in their entirety by reference.

BACKGROUND OF THE INVENTION

Compounds of Formula I, below

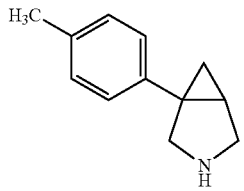

I including bicifadine, and salts and other forms of these compounds, are analgesics that are not narcotics (that is, are not morphine-like in action). See U.S. Pat. No. 4,231,935 and U.S. Pat. No. 4,196,120.

In administering a compound of Formula I to produce analgesia, it is important that the compound be administered in an effective manner to provide prompt and sustained activity through the presence of the compound in the blood system to effectively alleviate pain in the patient. There remains a significant, unmet need in the art for effective compositions and methods for delivering a compound of Formula I that will provide rapid relief of moderate and severe pain when administered and will maintain this relief for long periods of time.

SUMMARY OF EXEMPLARY EMBODIMENTS OF THE INVENTION

It is therefore an object of the present invention to provide novel and improved compositions, dosage forms, and methods employing a compound of Formula I, for example a bicifadine compound, to treat pain and improve functioning in mammalian subjects.

It is a further object of the invention to provide novel and improved compositions, dosage forms, and methods employing a compound of Formula I to treat or prevent one or more conditions of acute pain (e.g., pain resulting after major surgery and during recovery), chronic pain (e.g., chronic low back pain), and/or pain and other symptoms associated with neuropathic disorders, in mammalian subjects, and/or to approve functioning in subjects presenting with these conditions.

The invention achieves these objects and satisfies additional objects and advantages by providing new and surprisingly effective compositions, dosage forms, and methods employing a compound of Formula I in an effective formulation for treating acute pain, chronic pain, and/or pain or other symptoms associated with neuropathic disorders in mammals.

In one embodiment, the invention provides pharmaceutical compositions comprising a pre-determined dosage amount of an active compound of Formula I, which may be selected from, for example, bicifadine and pharmaceutically acceptable salts, enantiomers, polymorphs, solvates, hydrates, and prodrugs of bicifadine, and combinations thereof, in combination with a sustained release vehicle, matrix, binder or coating material. Following administration of this pharmaceutical composition to a mammalian treatment subject, the composition provides a mean maximum plasma concentration (Cmax) of the active compound in the treatment subject which is less than about 80% of a Cmax provided in a control subject after administration of the same amount of the active compound in an immediate release (IR) formulation.

In other embodiments of the invention, a composition comprising an active compound of Formula I (as used herein for shorthand, this reference to compounds of Formula I is intended to include all pharmaceutically acceptable salts, enantiomers, polymorphs, solvates, hydrates, and prodrugs of compounds that satisfy this formula) in combination with a sustained release vehicle, matrix, binder or coating material will provide, following administration of the composition to a mammalian treatment subject, a summated plasma concentration over time (referred to by those skilled in the art as Area Under the Curve (AUC)) of the active compound in the treatment subject which is less than about 80% of an AUC provided in a control subject following administration of the same amount of the active compound in an immediate release (IR) formulation.

In determining and comparing pharmacokinetic values according to the present description and examples below, including comparative AUC and Cmax values for SR and IR bicifadine formulations, standard procedures and statistical methods are employed. These standard procedures and statistical methods are well known in the art and may be found, for example, in FDA Guidance for Industry, Bioavailability and Bioequivalence Studies for Orally Administered Drug Products—General Considerations, CDER. October 2000; and FDA Guidance for Industry, Statistical Approaches to Establishing Bioequivalence (http://www.fda.gov/cder/guidance/index.htm; http://www.fda.gov/cder/guidance/3616fn-1.htm); and Fundamentals of Clinical Pharmacokinetics. J. G. Wagner, Drug Intelligence Publications, Inc., Hamilton, Ill., 1975 (each incorporated herein by reference). For example, in comparative pharmacokinetic studies presented herein, immediate-release (IR) oral dosage formulations of bicifadine are compared with exemplary sustained release (SR) oral dosage formulations using two-treatment, two-sequence, two-period crossover studies in healthy adult male and female human subjects. Metrics of peak (Cmax) and total (AUCt, AUCf) exposure are compared between bicifadine IR-dosed and SR-dosed subjects by analysis of variance (ANOVA) with effects for sequence, subject nested within sequence, period, and treatment. Confidence intervals (90%) are estimated around ratios (IR/SR) of least squares means derived from logarithmic-transformed metrics. Comparative Cmax and/or AUC value(s) produced in subjects after administration of an SR bicifadine formulation compared to the value(s) produced in subjects after administration of an IR bicifadine formulation is/are determined to be less than about 0.80 when the comparative data are evidenced by at least 90% confidence intervals.

Within additional embodiments of the invention, a composition comprising an active compound of Formula I in combination with a sustained release vehicle, matrix, binder, or coating material will provide, following administration of the composition to a mammalian treatment subject, a Cmax and an AUC of the active compound in the treatment subject which are each, respectively, less than about 80% of a Cmax and an AUC provided in a control subject following administration of the same amount of the active compound in an immediate release formulation.

The instant invention further provides novel methods for preventing or treating a condition or symptom of acute pain, chronic pain, and/or a neuropathic disorder in mammalian subjects. These methods involve administering to a treatment subject a pharmaceutical composition comprising a therapeutically effective amount of an active compound of Formula I (e.g., selected from bicifadine and pharmaceutically acceptable salts, enantiomers, polymorphs, solvates, hydrates, and prodrugs of bicifadine, and combinations thereof) combined with a sustained release vehicle, matrix, binder, or coating material. Following administration of this pharmaceutical composition to the treatment subject, a mean maximum plasma concentration (Cmax) of the active compound is obtained in the treatment subject which is less than about 80% of a Cmax obtained in a control subject after administration of the same amount of the active agent in an immediate release formulation. These methods surprisingly provide for prompt, long-lasting relief or prevention of the targeted condition or symptom of acute pain, chronic pain, or a neuropathic disorder in the subject without attendant, unacceptable adverse side effects. Within certain exemplary embodiments of the invention, the sustained release compositions and dosage forms described herein reduce the incidence and/or severity of one or more adverse side effects in treatment subjects compared to an incidence and/or severity of the same side effect(s) observed in subjects after administration of an equivalent amount of the active agent in an immediate release formulation.

Within additional embodiments of the invention, distinct methods for preventing or treating a condition or symptom of chronic pain in mammalian subjects are provided. These chronic pain treatment methods involve administering to the subject an active compound of Formula I (e.g., selected from bicifadine and pharmaceutically acceptable salts, enantiomers, polymorphs, solvates, hydrates, and prodrugs of bicifadine, and combinations thereof), in a daily dosing regimen consisting of only one or two doses of the active compound per day, which is surprisingly effective to alleviate or prevent the targeted chronic pain condition or symptom in the subject, without attendant, unacceptable adverse side effects, over an extended period, e.g., up to a 24 hour period. Within alternate embodiments of this aspect of the invention, a once daily or twice daily dosing protocol is provided which employs either an immediate release, controlled release, or sustained release formulation, which is effective for treating the chronic pain over an extended period. Within certain exemplary embodiments, a sustained release composition or dosage form as described herein is employed in a method for treating chronic pain involving a limited dosing schedule of once or twice daily administration, wherein an incidence and/or severity of one or more adverse side effects is reduced in treatment subjects compared to an incidence and/or severity of the same side effect(s) observed in subjects after administration of an equivalent amount of the active agent in an immediate release formulation.

DETAILED DESCRIPTION OF EXEMPLARY EMBODIMENTS OF THE INVENTION

Figure 1:
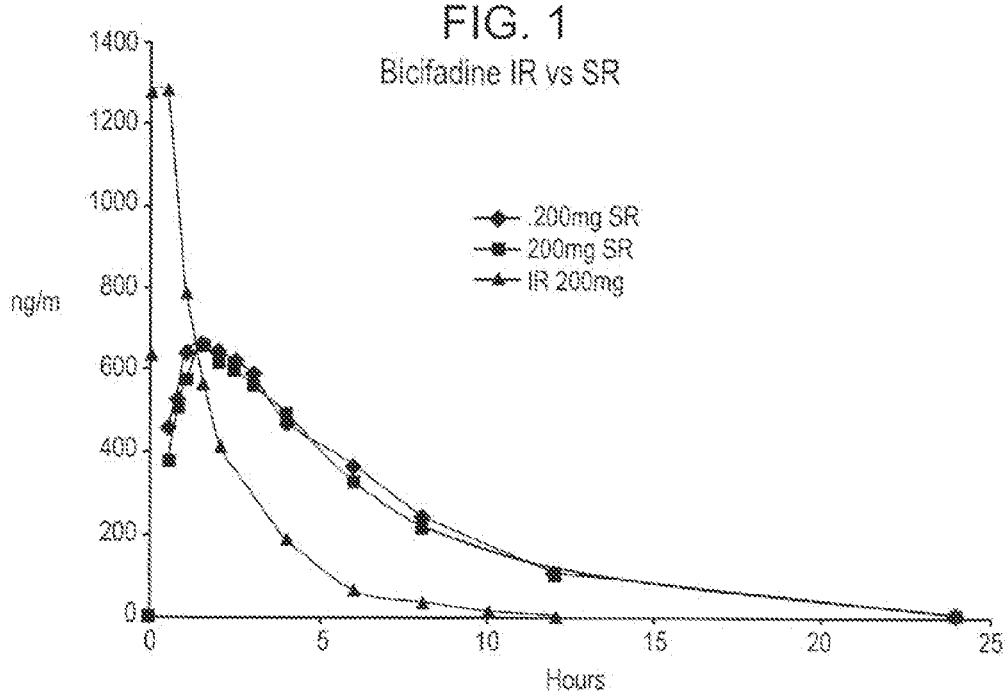
FIG. 1 illustrates plasma concentration time course data for exemplary bicifadine immediate release (IR) and sustained release (SR) formulations.

The instant invention provides novel compositions, dosage forms and methods for treating symptoms of acute pain, chronic pain, and/or a neuropathic disorder in mammalian subjects. The compositions and methods of the invention employ a pre-determined, therapeutically effective dosage amount of an active therapeutic compound of Formula I, below, formulated in a sustained release composition or dosage form.

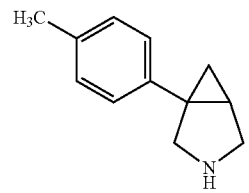

In exemplary embodiments, the compound of Formula I is selected from bicifadine (e.g., a free base form of bicifadine) and pharmaceutically acceptable salts, enantiomers, polymorphs, solvates, hydrates, and prodrugs of bicifadine, and combinations thereof.

Within exemplary compositions and dosage forms of the invention, the compound of Formula I is combined with a sustained release vehicle, matrix, binder, or coating material. As used herein, the term "sustained release vehicle, matrix, binder, or coating material" refers to any vehicle, matrix, binder, or coating material that effectively, significantly delays dissolution of the active compound in vitro, and/or delays, modifies, or extends delivery of the active compound into the blood stream (or other in vivo target site of activity) of a subject following administration (e.g., oral administration), in comparison to dissolution and/or delivery provided by an "immediate release" formulation, as described herein, of the same dosage amount of the active compound. Accordingly, the term "sustained release vehicle, matrix, binder, or coating material" as used herein is intended to include all such vehicles, matrices, binders and coating materials known in the art as "sustained release", "delayed release", "slow release", "extended release", "controlled release", "modified release", and "pulsatile release" vehicles, matrices, binders and coatings.

In one aspect, the current invention comprises an oral sustained release dosage composition for administering an active compound of Formula I. In a related aspect, the invention comprises a method of reducing one or more side effects that attend administration of an oral dosage forms of a compound of Formula I. Within these methods, the compound of Formula I is provided in a sustained release oral dosage form and the dosage form is introduced into a gastrointestinal tract of a mammalian subject presenting with acute pain, chronic pain, or a neuropathic disorder, by having the subject swallow the dosage form. The method further includes releasing the active compound of Formula I in a sustained, delayed, gradual or modified release delivery mode into the gastrointestinal tract (e.g., the intestinal lumen) of the subject over a period of hours, during which the active compound reaches, and is sustained at, a therapeutic concentration in a blood plasma, tissue, organ or other target site of activity (e.g., a central nervous system (CNS) tissue, fluid or compartment) in the patient. When following this method, the side effect profile of the active compound is less than a side effect profile of an equivalent dose of the active compound administered in an immediate release oral dosage form.

In certain embodiments, the active compound of Formula I is released from the sustained release compositions and dosage forms of the invention and delivered into the blood plasma or other target site of activity in the subject at a sustained therapeutic level over a period of at least about 6 hours, often over a period of at least about 8 hours, at least about 12 hours, or at least about 18 hours, and in other embodiments over a period of about 24 hours or greater. By sustained therapeutic level is meant a plasma concentration level of at least about 400-500 ng/ml or greater. In more detailed embodiments of the invention, the sustained release compositions and dosage forms will yield a therapeutic level of a compound of Formula I following administration to a mammalian subject in a desired dosage amount (e.g., 200, 400, 600, or 800 mg) that yields a minimum plasma concentration of greater than 500 ng/ml over a period of at least about 6 hours, at least about 8 hours, at least about 12 hours, at least about 18 hours, or up to 24 hours or longer. In alternate embodiments of the invention, the sustained release compositions and dosage forms will yield a therapeutic level of a compound of Formula I following administration to a mammalian subject in a desired dosage amount (e.g., 200, 400, 600, or 800 mg) that yields a minimum plasma concentration of greater than 600 ng/ml, greater than 700 ng/ml, greater than 800 ng/ml, or greater than 900 ng/ml over a period of at least about 6 hours, at least about 8 hours, at least about 12 hours, at least about 18 hours, or up to 24 hours or longer.

In certain embodiments, the active compound of Formula I is released from the compositions and dosage forms of the invention and delivered into the blood plasma or other target site of activity in the subject in a sustained release profile characterized in that from about 0% to 20% of the active compound is released and delivered (as determined, e.g., by measuring blood plasma levels) within in 0 to 2 hours, from 20% to 50% of the active compound is released and delivered within about 2 to 12 hours, from 50% to 85% of the active compound is released and delivered within about 3 to 20 hours, and greater than 75% of the active compound is released and delivered within about 5 to 18 hours.

In more detailed embodiments of the invention, compositions and oral dosage forms of a compound of Formula I are provided, wherein the compositions and dosage forms, after ingestion, provide a curve of concentration of the active compound over time, the curve having an area under the curve (AUC) which is approximately proportional to the dose of the active compound administered, and a maximum concentration (Cmax) that is proportional to the dose of the active compound administered.

In other detailed embodiments, the Cmax of the active compound of Formula I provided after oral delivery of a composition or dosage form of the invention is less than about 80%, often less than about 75%, in some embodiments less than about 60%, or 50%, of a Cmax obtained after administering an equivalent dose of the active compound in an immediate release oral dosage form.

In other detailed embodiments, the AUC of the active compound of Formula I provided after oral delivery of a composition or dosage form of the invention is less than about 80%, often less than about 75%, in some embodiments less than about 60%, or 50%, of a AUC obtained after administering an equivalent dose of the active compound in an immediate release oral dosage form.

In other detailed embodiments, each of the Cmax and AUC of the active compound of Formula I provided after oral delivery of a composition or dosage form of the invention is less than about 80%, often less than about 75%, in some embodiments less than about 60%, or 50%, of a Cmax and AUC obtained after administering an equivalent dose of the active compound in an immediate release oral dosage form.

Within exemplary embodiments of the invention, the compositions and dosage forms containing the active compound of Formula I and a sustained release vehicle, matrix, binder, or coating will yield sustained delivery of the active compound such that, following administration of the composition or dosage form to a mammalian treatment subject, the Cmax of the active compound in the treatment subject is less than about 80% of a Cmax provided in a control subject after administration of the same amount of the active agent in an immediate release formulation.

Within other exemplary embodiments of the invention, the compositions and dosage forms containing the active compound of Formula I and a sustained release vehicle, matrix, binder, or coating will yield sustained delivery of the active compound such that, following administration of the composition or dosage form to a mammalian treatment subject, the AUC of the active compound in the treatment subject is less than about 80% of a AUC provided in a control subject after administration of the same amount of the active agent in an immediate release formulation.

Within additional exemplary embodiments, the compositions and dosage forms containing the active compound of Formula I and a sustained release vehicle, matrix, binder, or coating will yield sustained delivery of the active compound such that, following administration of the composition or dosage form to a mammalian treatment subject, the Cmax and AUC of the active compound in the treatment subject are, respectively, less than about 80% of a Cmax and a AUC provided in a control subject after administration of the same amount of the active agent in an immediate release formulation.

As used herein, the term "immediate release dosage form" refers to a dosage form of an active compound of Formula I wherein the active compound readily dissolves upon contact with a liquid physiological medium, for example phosphate buffered saline (PBS) or natural or artificial gastric fluid. In certain embodiments, an IR formulation will be characterized in that at least 70% of the active compound will be dissolved within a half hour after the dosage form is contacted with a liquid physiological medium. For example, at least 70% of the active compound in an IR bicifadine dosage form will dissolve within a half hour following contact of the dosage form with a liquid physiological medium in an art-accepted in vitro dissolution assay (e.g., using a USP 1 Apparatus, 20 mesh baskets, 75 rpm, and a dissolution medium comprised of 900 ml 0.01 N HCl at 37° C.±0.5° C.; or following an alternate USP basket method at 100 rpm in 700 ml Simulated Gastric Fluid (SGF) at 37° C. for 1 hour and thereafter switching to 900 ml with phosphate buffer to a pH of 7.5 at 37° C.). In alternate embodiments, at least 80%, 85%, 90% or more, or up to 100%, of the active compound in an IR bicifadine dosage form will dissolve within a half hour following contact of the dosage form with a liquid physiological medium in an art-accepted in vitro dissolution assay. These general characteristics of an IR dosage form will often relate to powdered or granulated compositions of a compound of Formula I in a capsulated dosage form, for example in a gelatin-encapsulated dosage form, where dissolution will often be relatively immediate after dissolution/failure of the gelatin capsule. In alternate embodiments, the IR dosage form may be provided in the form of a compressed tablet, granular preparation, powder, or even liquid dosage form, in which cases the dissolution profile will often be even more immediate (e.g., wherein at least 85%-95% of the active compound is dissolved within a half hour).

In additional embodiments of the invention, an IR dosage form will include compositions wherein the active compound is not admixed, bound, coated or otherwise associated with a formulation component that substantially impedes in vitro or in vivo dissolution and/or in vivo bioavailability of the active compound. Within certain embodiments, the active compound will be provided in an immediate release dosage form that does not contain significant amounts of a sustained release vehicle, matrix, binder or coating material. In this context, the term "significant amounts of a sustained release vehicle, matrix, binder or coating material" is not intended to exclude any amount of such materials, but an amount sufficient to impede in vitro or in vivo dissolution of an active compound in a formulation containing such materials by at least 5%, often at least 10%, and up to at least 15%-20% compared to dissolution of the active compound when provided in a composition that is essentially free of such materials.

In alternate embodiments of the invention, an IR dosage form of a compound of Formula I may be any dosage form comprising the active compound which fits the FDA Biopharmaceutics Classification System (BCS) Guidance definition (see, e.g., http://www.fda.gov/cder/OPS/BCS_guidance.htm) of a "high solubility substance in a rapidly dissolving formulation". In exemplary embodiments, an IR bicifadine formulation according to this aspect of the invention will exhibit rapid dissolution characteristics according to BCS Guidance parameters, such that at least approximately 85% of the bicifadine in the formulation will go into a test solution within about 30 minutes at pH 1, pH 4.5, and pH 6.8.

In yet additional embodiments of the invention, an IR dosage form of a compound of Formula I may be any of the IR dosage forms specifically described herein.

The compositions, dosage forms and methods of the invention are thus characterized and distinguished as novel tools for treatment of pain and neuropathic disorders by virtue that they provide for sustained release and/or sustained delivery of the active compounds of Formula I. As used herein, "sustained release" and "sustained delivery" are evinced by a sustained, delayed, extended, or modified, in vitro or in vivo dissolution rate, in vivo release and/or delivery rate, and/or in vivo pharmacokinetic value(s) or profile. Within exemplary embodiments of the invention, the sustained release and sustained delivery compositions and dosage forms of the invention will exhibit less than about 80% of one or more release/delivery property(ies) value(s) or range(s) selected from i) an in vitro dissolution rate, ii) in vivo dissolution or release rate, and/or iii) plasma Cmax, AUC, and/or Cmax and AUC, exhibited by an otherwise comparable, immediate release composition or dosage form of the active compound. Often, the one or more release/delivery property(ies) selected from i) an in vitro dissolution rate, ii) in vivo dissolution or release rate, and/or iii) plasma Cmax, AUC, and/or Cmax and AUC of the sustained release compositions and dosage forms of the invention will be less than about 75%, in some embodiments less than about 60%, or 50%, of the respective release/delivery property(ies) of an otherwise comparable, immediate release dosage form of the active compound. The terms "sustained release" and "sustained delivery" are intended herein to encompass release and delivery properties conventionally known in the art as "sustained", "delayed", "slow", "extended", "controlled", "modified", and "pulsatile" release and delivery.

The sustained release dosage forms of the present invention can take any form as long as one or more of the dissolution, release, delivery and/or pharmacokinetic property(ies) identified above are satisfied. Within illustrative embodiments, the composition or dosage form can comprise the active compound of Formula I combined with any one or combination of: a drug-releasing polymer, matrix, bead, microcapsule, or other solid drug-releasing vehicle; drug-releasing tiny timed-release pills or mini-tablets; compressed solid drug delivery vehicle; controlled release binder; multi-layer tablet or other multi-layer or multi-component dosage form; drug-releasing lipid; drug-releasing wax; and a variety of other sustained drug release materials as contemplated herein, or formulated in an osmotic dosage form.

The present invention thus provides a broad range of sustained release compositions and dosage forms comprising an active compound of Formula I, which in certain embodiments are adapted for providing sustained release of the active compound following, e.g., oral administration. Sustained release vehicles, matrices, binders and coatings for use in accordance with the invention include any biocompatible sustained release material which is inert to the active agent and which is capable of being physically combined, admixed, or incorporated with the active compound. Useful sustained release materials may be dissolved, degraded, disintegrated, and/or metabolized slowly under physiological conditions following delivery (e.g., into a gastrointestinal tract of a subject, or following contact with gastric fluids or other bodily fluids). Useful sustained release materials are typically non-toxic and inert when contacted with fluids and tissues of mammalian subjects, and do not trigger significant adverse side effects such as irritation, immune response, inflammation, or the like. They are typically metabolized into metabolic products which are biocompatible and easily eliminated from the body.

In certain embodiments, sustained release polymeric materials are employed as the sustained release vehicle, matrix, binder, or coating (see, e.g., "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, N.Y. (1984); Ranger and Peppas, 1983, J. Macromol. Sci. Rev. Macromol Chem. 23:61; see also Levy et al., 1985, Science 228: 190; During et al., 1989, Ann. Neurol. 25:351; Howard et al, 1989, J. Neurosurg. 71:105, each incorporated herein by reference). Within exemplary embodiments, useful polymers for co-formulating with the active compound of Formula I to yield a sustained release composition or dosage form include, but are not limited to, ethylcellulose, hydroxyethyl cellulose; hydroxyethylmethyl cellulose; hydroxypropyl cellulose; hydroxypropylmethyl cellulose; hydroxypropylmethyl cellulose phthalate; hydroxypropylmethylcellulose acetate succinate; hydroxypropylmethylcellulose acetate phthalate; sodium carboxymethylcellulose; cellulose acetate phthalate; cellulose acetate trimellitate; polyoxyethylene stearates; polyvinyl pyrrolidone; polyvinyl alcohol; copolymers of polyvinyl pyrrolidone and polyvinyl alcohol; polymethacrylate copolymers; and mixtures thereof.

Additional polymeric materials for use as sustained release vehicles, matrices, binders, or coatings within the compositions and dosage forms of the invention include, but are not limited to, additional cellulose ethers, e.g., as described in Alderman, Int. J. Pharm. Tech. & Prod. Mfr., 1984, 5(3) 1-9 (incorporated herein by reference). Other useful polymeric materials and matrices are derived from copolymeric and homopolymeric polyesters having hydrolysable ester linkages. A number of these are known in the art to be biodegradable and to lead to degradation products having no or low toxicity. Exemplary polymers in this context include polyglycolic acids (PGAs) and polylactic acids (PLAs), poly(DL-lactic acid-co-glycolic acid) (DL PLGA), poly(D-lactic acid-coglycolic acid) (D PLGA) and poly(L-lactic acid-co-glycolic acid) (L PLGA). Other biodegradable or bioerodable polymers for use within the invention include such polymers as poly($\epsilon$-caprolactone), poly($\epsilon$-aprolactone-CO-lactic acid), poly($\epsilon$-aprolactone-CO-glycolic acid), poly($\beta$-hydroxy butyric acid), poly(alkyl-2-cyanoacrilate), hydrogels such as poly(hydroxyethyl methacrylate), polyamides, poly-amino acids (e.g., poly-L-leucine, poly-glutamic acid, poly-L-aspartic acid, and the like), poly (ester ureas), poly (2-hydroxyethyl DL-aspartamide), polyacetal polymers, polyorthoesters, polycarbonates, polymaleamides, polysaccharides, and copolymers thereof. Methods for preparing pharmaceutical formulations using these polymeric materials are generally known to those skilled in the art (see, e.g., *Sustained and Controlled Release Drug Delivery Systems*, J. R. Robinson, ed., Marcel Dekker, Inc., New York, 1978, incorporated herein by reference).

In other embodiments of the invention, the compositions and dosage forms comprise an active compound of Formula I coated on a polymer substrate. The polymer can be an erodible or a nonerodible polymer. The coated substrate may be folded onto itself to provide a bilayer polymer drug dosage form. For example an active compound of Formula I can be coated onto a polymer such as a polypeptide, collagen, gelatin, polyvinyl alcohol, polyorthoester, polyacetyl, or a poly-orthocarbonate, and the coated polymer folded onto itself to provide a bilaminated dosage form. In operation, the bioerodible dosage form erodes at a controlled rate to dispense the active compound over a sustained release period. Representative biodegradable polymers for use in this and other aspects of the invention can be selected from, for example, biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly(dehydropyrans), and poly(dioxinones) which are known in the art (see, e.g., Rosoff, Controlled Release of Drugs, Chap. 2, pp. 53-95 (1989); and U.S. Pat. Nos. 3,811,444; 3,962,414; 4,066,747, 4,070,347; 4,079,038; and 4,093,709, each incorporated herein by reference).

In another embodiment of the invention, the dosage form comprises an active compound of Formula I loaded into a polymer that releases the prodrug by diffusion through a polymer, or by flux through pores or by rupture of a polymer matrix. The drug delivery polymeric dosage form comprises the active compound contained in or on the polymer. The dosage form comprises at least one exposed surface at the beginning of dose delivery. The non-exposed surface, when present, can be coated with a pharmaceutically acceptable material impermeable to the passage of a drug. The dosage form may be manufactured by procedures known in the art, for example by blending a pharmaceutically acceptable carrier like polyethylene glycol, with a pre-determined dose of the active compound at an elevated temperature (e.g., 37° C.), and adding it to a silastic medical grade elastomer with a cross-linking agent, for example, octanoate, followed by casting in a mold. The step is repeated for each optional successive layer. The system is allowed to set for 1 hour, to provide the dosage form. Representative polymers for manufacturing such sustained release dosage forms include, but are not limited to, olefin, and vinyl polymers, addition polymers, condensation polymers, carbohydrate polymers, and silicon polymers as represented by polyethylene, polypropylene, polyvinyl acetate, polymethylacrylate, polyisobutylmethacrylate, poly alginate, polyamide and polysilicon. These polymers and procedures for manufacturing them have been described in the art (see, e.g., Coleman et al., Polymers 1990, 31, 1187-1231; Roerdink et al., Drug Carrier Systems 1989, 9, 57-10; Leong et al., Adv. Drug Delivery Rev. 1987, 1, 199-233; and Roff et al., Handbook of Common Polymers 1971, CRC Press; U.S. Pat. No. 3,992,518).

In other embodiments of the invention, the compositions and dosage forms comprise an active compound of Formula I incorporated with or contained in beads that on dissolution or diffusion release the active compound over an extended period of hours, for example over a period of at least 6 hours, over a period of at least 8 hours, over a period of at least 12 hours, or over a period of up to 24 hours or longer. The drug-releasing beads may have a central composition or core comprising an active compound of Formula I and a pharmaceutically acceptable carrier, along with one or more optional excipients such as a lubricants, antioxidants, dispersants, and buffers. The beads may be medical preparations with a diameter of about 1 to 2 mm. In exemplary embodiments the are formed of non-cross-linked materials to enhance their discharge from the gastrointestinal tract. The beads may be coated with a release rate-controlling polymer that gives a timed release pharmacokinetic profile. In alternate embodiments the beads may be manufactured into a tablet for therapeutically effective drug administration. The beads can be made into matrix tablets by direct compression of a plurality of beads coated with, for example, an acrylic resin and blended with excipients such as hydroxypropylmethyl cellulose. The manufacture and processing of beads for use within the invention is described in the art (see, e.g., Lu, Int. J. Pharm., 1994, 112, 117-124; Pharmaceutical Sciences by Remington, 14.sup.th ed, pp 1626-1628 (1970); Fincher, J. Pharm. Sci. 1968, 57, 1825-1835; and U.S. Pat. No. 4,083,949, each incorporated by reference) as has the manufacture of tablets (Pharmaceutical Sciences, by Remington, 17$^{th}$ Ed, Ch. 90, pp 1603-1625, 1985, incorporated herein by reference).

In another embodiment of the invention, the dosage from comprises a plurality of tiny pills or mini-tablets. The tiny pills or mini-tablets provide a number of individual doses for providing various time doses for achieving a sustained-release drug delivery profile over an extended period of time up to 24 hours. The tiny pills or mini-tablets may comprise a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, and a hydrophilic colloid. The hydrophilic polymer may be formed into a plurality (e.g., 4 to 50) tiny pills or mini-tablet, wherein each tiny pill or mini-tablet comprises a predetermined dose of the active compound of Formula I, e.g., a dose of about 10 ng, 0.5 mg, 1 mg, 1.2 mg, 1.4 mg, 1.6 mg, 5.0 mg etc. The tiny pills and mini-tablets may further comprise a release rate-controlling wall of 0.001 up to 10 mm thickness to provide for timed release of the active compound. Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills and mini-tablets are known in the art (see, e.g., U.S. Pat. Nos. 4,434,153; 4,721,613; 4,853,229; 2,996,431; 3,139,383 and 4,752,470, each incorporated herein by reference). The tiny pills and mini-tablets may further comprise a blend of particles, which may include particles of different sizes and/or release properties, and the particles may be contained in a hard gelatin or non-gelatin capsule or soft gelatin capsule.

In yet another embodiment of the invention, drug-releasing lipid matrices can be used to formulate therapeutic compositions and dosage forms comprising an active compound of Formula I. In one exemplary embodiment, solid microparticles of the active compound are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700 (each incorporated herein by reference). The lipid-coated particles can optionally be compressed to form a tablet. Another controlled release lipid-based matrix material which is suitable for use in the sustained release compositions and dosage forms of the invention comprises polyglycolized glycerides, e.g., as described in Roussin et al., U.S. Pat. No. 6,171,615 (incorporated herein by reference).

In other embodiments of the invention, drug-releasing waxes can be used for producing sustained release compositions and dosage forms comprising an active compound of Formula I. Examples of suitable sustained drug-releasing waxes include, but are not limited to, carnauba wax, candedilla wax, esparto wax, ouricury wax, hydrogenated vegetable oil, bees wax, paraffin, ozokerite, castor wax, and mixtures thereof (see, e.g., Cain et al., U.S. Pat. No. 3,402,240; Shtohryn et al. U.S. Pat. No. 4,820,523; and Walters, U.S. Pat. No. 4,421,736, each incorporated herein by reference).

In still another embodiment, osmotic delivery systems are used for sustained release delivery of an active compound of Formula I (see, e.g., Verma et al., Drug Dev. Ind. Pharm., 2000, 26:695-708, incorporated herein by reference). In one exemplary embodiment, the osmotic delivery system is an OROS® system (Alza Corporation, Mountain View, Calif.) and is adapted for oral sustained release delivery of drugs (see, e.g., U.S. Pat. No. 3,845,770; and U.S. Pat. No. 3,916,899, each incorporated herein by reference).

In another embodiment of the invention, the dosage form comprises an osmotic dosage form, which comprises a semipermeable wall that surrounds a therapeutic composition comprising the prodrug. In use within a patient, the osmotic dosage form comprising a homogenous composition imbibes fluid through the semipermeable wall into the dosage form in response to the concentration gradient across the semipermeable wall. The therapeutic composition in the dosage form develops osmotic energy that causes the therapeutic composition to be administered through an exit from the dosage form over a prolonged period of time up to 24 hours (or even in some cases up to 30 hours) to provide controlled and sustained prodrug release. These delivery platforms can provide an essentially zero order delivery profile as opposed to the spiked profiles of immediate release formulations.

In alternate embodiments of the invention, the dosage form comprises another osmotic dosage form comprising a wall surrounding a compartment, the wall comprising a semipermeable polymeric composition permeable to the passage of fluid and substantially impermeable to the passage of the active compound present in the compartment, a drug-containing layer composition in the compartment, a hydrogel push layer composition in the compartment comprising an osmotic formulation for imbibing and absorbing fluid for expanding in size for pushing the prodrug composition layer from the dosage form, and at least one passageway in the wall for releasing the prodrug composition. This osmotic system delivers the active compound by imbibing fluid through the semipermeable wall at a fluid imbibing rate determined by the permeability of the semipermeable wall and the osmotic pressure across the semipermeable wall causing the push layer to expand, thereby delivering the active compound through the exit passageway to a patient over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer may comprise a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxypentylcellulose), an osmagent, e.g., selected from the group consisting of sodium chloride, potassium chloride, potassium acid phosphate, tartaric acid, citric acid, raffinose, magnesium sulfate, magnesium chloride, urea, inositol, sucrose, glucose and sorbitol, and other agents such a hydroxypropylalkylcellulose of 9,000 to 225,000 average-number molecular weight (e.g., hydroxypropylethylcellulose, hydroxypropypentylcellulose, hydroxypropylmethylcellulose, or hydropropylbutylcellulose), ferric oxide, antioxidants (e.g., ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propyl-hydroxybenzoate, trihydroxybutylrophenone, dimethylphenol, dibutylphenol, vitamin E, lecithin and ethanolamine), and/or lubricants (e.g., calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid).

In the osmotic dosage forms, the semipermeable wall comprises a composition that is permeable to the passage of fluid and impermeable to passage of the active compound of Formula I. The wall is nontoxic and comprises a polymer selected from the group consisting of a cellulose acylate, cellulose diacylate, cellulose triacylate, cellulose acetate, cellulose diacetate and cellulose triacetate. The wall typically comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether (e.g., hydroxypropylcellulose or a hydroxypropylalkycellulose such as hydroxypropylmethylcellulose). The total weight percent of all components comprising the wall is equal to 100 wt %. The internal compartment comprises the drug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of prodrug to a patient over time. The dosage form comprises a passageway in the wall that connects the exterior of the dosage form with the internal compartment. The osmotic powered dosage form delivers the active compound of Formula I from the dosage form to the patient at a zero order rate of release over a period of up to about 24 hours. As used herein, the expression "passageway" comprises means and methods suitable for the metered release of an active compound of Formula I from the compartment of an osmotic dosage form. The exit means comprises at least one passageway, including orifice, bore, aperture, pore, porous element, hollow fiber, capillary tube, channel, porous overlay, or porous element that provides for the osmotic controlled release of the active compound. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of prodrug from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916,899; 4,063, 064; 4,088,864; 4,816,263; 4,200,098; and 4,285,987 (each incorporated herein by reference).

Within other aspects of the invention, microparticle, microcapsule, and/or microsphere drug delivery technologies can be employed to provide sustained release delivery of an active compound of Formula I within the compositions, dosage forms and methods of the invention. A variety of methods is known by which an active compound of Formula I can be encapuslated in the for of microparticles, for example using by encapsulating the active compound within a biocompatible, biodegradable wall-forming material (e.g., a polymer)— to provide sustained or delayed release of the active compound. In these methods, the active compound is typically dissolved, dispersed, or emulsified in a solvent containing the wall forming material. Solvent is then removed from the microparticles to form the finished microparticle product. Examples of conventional microencapsulation processes are disclosed, e.g., in U.S. Pat. Nos. 3,737,337; 4,389,330; 4,652, 441; 4,917,893; 4,677,191; 4,728,721; 5,407,609; 5,650,173; 5,654,008; and 6,544,559 (each incorporated herein by reference). These documents disclose methods that can be readily implemented to prepare microparticles containing an active compound of Formula I in a sustained release formulation according to the invention. As explained, for example, in U.S. Pat. No. 5,650,173, by appropriately selecting the polymeric materials, a microparticle formulation can be made in which the resulting microparticles exhibit both diffusional release and biodegradation release properties. For a diffusional mechanism of release, the active agent is released from the microparticles prior to substantial degradation of the polymer. The active agent can also be released from the microparticles as the polymeric excipient erodes. In addition, U.S. Pat. No. 6,596,316 (incorporated herein by reference) discloses methods for preparing microparticles having a selected release profile for fine tuning a release profile of an active agent from the microparticles.

In another embodiment of the invention, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release). Enteric coatings may function as a means for mediating sustained release of the active compound of Formula I by providing one or more barrier layers, which may be located entirely surrounding the active compound, between layers of a multi-layer solid dosage form (see below), and/or on one or more outer surfaces of one or multiple layers of a multi-layer solid dosage form (e.g., on end faces of layers of a substantially cylindrical tablet). Such barrier layers may, for example, be composed of polymers which are either substantially or completely impermeable to water or aqueous media, or are slowly erodible in water or aqueous media or biological liquids and/or which swell in contact with water or aqueous media. Suitable polymers for use as a barrier layer include acrylates, methacrylates, copolymers of acrylic acid, celluloses and derivatives thereof such as ethylcelluloses, cellulose acetate propionate, polyethylenes and polyvinyl alcohols etc. Barrier layers comprising polymers which swell in contact with water or aqueous media may swell to such an extent that the swollen layer forms a relatively large swollen mass, the size of which delays its immediate discharge from the stomach into the intestine. The barrier layer may itself contain active material content, for example the barrier layer may be a slow or delayed release layer. Barrier layers may typically have an individual thickness of 10 microns up to 2 mm. Suitable polymers for barrier layers which are relatively impermeable to water include the Methocel™ series of polymers, used singly or combined, and Ethocel™ polymers. Such polymers may suitably be used in combination with a plasticiser such as hydrogenated castor oil. The barrier layer may also include conventional binders, fillers, lubricants and compression acids etc such as Polyvidon K30 (trade mark), magnesium stearate, and silicon dioxide.

Additional enteric coating materials for mediating sustained release of an active compound of Formula I include coatings in the form of polymeric membranes, which may be semipermeable, porous, or asymmetric membranes (see, e.g., U.S. Pat. No. 6,706,283, incorporated herein by reference). Coatings of these and other types for use within the invention may also comprise at least one delivery port, or pores, in the coating, e.g., formed by laser drilling or erosion of a plug of water-soluble material. Other useful coatings within the invention including coatings that rupture in an environment of use (e.g., a gastrointestinal compartment) to form a site of release or delivery port. Exemplar coatings within these and other embodiments of the invention include poly(acrylic) acids and esters; poly(methacrylic) acids and esters; copolymers of poly(acrylic) and poly(methacrylic) acids and esters; cellulose esters; cellulose ethers; and cellulose ester/ethers.

Additional coating materials for use in constructing solid dosage forms to mediate sustained release of an active compound of Formula I include, but are not limited to, polyethylene glycol, polypropylene glycol, copolymers of polyethylene glycol and polypropylene glycol, poly(vinylpyrrolidone), ethyl cellulose, hydroxyethyl cellulose, hydroxypropyl cellulose, carboxymethyl cellulose, carboxymethylethyl cellulose, starch, dextran, dextrin, chitosan, collagen, gelatin, bromelain, cellulose acetate, unplasticized cellulose acetate, plasticized cellulose acetate, reinforced cellulose acetate, cellulose acetate phthalate, cellulose acetate trimellitate, hydroxypropylmethylcellulose, hydroxypropylmethyl-cellulose phthalate, hydroxypropylmethylcellulose acetate succinate, hydroxypropylmethylcellulose acetate trimellitate, cellulose nitrate, cellulose diacetate, cellulose triacetate, agar acetate, amylose triacetate, beta glucan acetate, beta glucan triacetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate propionate, cellulose acetate p-toluene sulfonate, triacetate of locust gum bean, cellulose acetate with acetylated hydroxyethyl cellulose, hydroxlated ethylene-vinylacetate, cellulose acetate butyrate, polyalkenes, polyethers, polysulfones, polyethersulfones, polystyrenes, polyvinyl halides, polyvinyl esters and ethers, natural waxes and synthetic waxes.

In additional embodiments of the invention, sustained release of the active compound of Formula I is provided by formulating the active compound in a dosage form comprising a multi-layer tablet or other multi-layer or multi-component dosage form. In exemplary embodiments, the active compound is formulated in layered tablets, for example having a first layer which is an immediate release layer and a second layer which is a slow release layer. Other multi-layered dosage forms of the invention may comprise a plurality of layers of compressed active ingredient having variable (i.e., selectable) release properties selected from immediate, extended and/or delayed release mechanisms. Multi-layered tablet technologies useful to produce sustained release dosage forms of an active compound of Formula I are described, for example, in International Publications WO 95/20946; WO 94/06416; and WO 98/05305 (each incorporated herein by reference). Other multi-component dosage forms for providing sustained delivery of an active compound of Formula I include tablet formulations having a core containing the active compound clavulanate coated with a release retarding agent and surrounded by an outer casing layer (optionally containing the active compound) (see, e.g., International Publication WO 95/28148, incorporated herein by reference). The release retarding agent is an enteric coating, so that there is an immediate release of the contents of the outer core, followed by a second phase from the core which is delayed until the core reaches the intestine. Additionally, International Publication WO 96/04908 (incorporated herein by reference) describes tablet formulations which comprise an active agent in a matrix, for immediate release, and granules in a delayed release form comprising the active agent. Such granules are coated with an enteric coating, so release is delayed until the granules reach the intestine. International Publication WO 96/04908 (incorporated herein by reference) describes delayed or sustained release formulations formed from granules which have a core comprising an active agent, surrounded by a layer comprising the active agent.

Another useful multi-component (bi-layer tablet) dosage form for sustained delivery of active compounds of Formula I is described in U.S. Pat. No. 6,878,386 (incorporated herein by reference). Briefly, the bilayer tablet comprises an immediate release and a slow release layer, optionally with a coating layer. The immediate release layer may be, for example, a layer which disintegrates immediately or rapidly and has a composition similar to that of known tablets which disintegrate immediately or rapidly. An alternative type of immediate release layer may be a swellable layer having a composition which incorporates polymeric materials which swell immediately and extensively in contact with water or aqueous media, to form a water permeable but relatively large swollen mass. Active material content may be immediately leached out of this mass. The slow release layer may have a composition comprising the active compound of Formula I with a release retarding vehicle, matrix, binder, coating, or excipient which allows for slow release of the active compound. Suitable release retarding excipients include pH sensitive polymers, for instance polymers based upon methacrylic acid copolymers, which may be used either alone or with a plasticiser; release-retarding polymers which have a high degree of swelling in contact with water or aqueous media such as the stomach contents; polymeric materials which form a gel on contact with water or aqueous media; and polymeric materials which have both swelling and gelling characteristics in contact with water or aqueous media. Release retarding polymers which have a high degree of swelling include, inter alia, cross-linked sodium carboxymethylcellulose, cross-linked hydroxypropylcellulose, high-molecular weight hydroxypropylmethylcellulose, carboxymethylamide, potassium methacrylatedivinylbenzene co-polymer, polymethylmethacrylate, cross-linked polyvinylpyrrolidone, high-molecular weight polyvinylalcohols etc. Release retarding gellable polymers include methylcellulose, carboxymethylcellulose, low-molecular weight hydroxypropylmethylcellulose, low-molecular weight polyvinylalcohols, polyoxyethyleneglycols, non-cross linked polyvinylpyrrolidone, xanthan gum etc. Release retarding polymers simultaneously possessing swelling and gelling properties include medium-viscosity hydroxypropylmethylcellulose and medium-viscosity polyvinylalcohols. An exemplary release-retarding polymer is xanthan gum, in particular a fine mesh grade of xanthan gum, preferably pharmaceutical grade xanthan gum, 200 mesh, for instance the product Xantural 75 (also known as Keltrol CR™ Monsanto, 800 N Lindbergh Blvd, St Louis, Mo. 63167, USA). Xanthan gum is a polysaccharide which upon hydration forms a viscous gel layer around the tablet through which the active has) to diffuse. It has been shown that the smaller the particle size, the slower the release rate. In addition, the rate of release of active compound is dependent upon the amount of xanthan gum used and can be adjusted to give the desired profile. Examples of other polymers which may be used within these aspects of the invention include Methocel K4M™, Methocel E5™, Methocel E50™, Methocel E4M™, Methocel K15M™ and Methocel K100M™. Other known release-retarding polymers which may be incorporated within this and other embodiments of the invention to provide a sustained release composition or dosage form of an active compound of Formula I include, hydrocolloids such as natural or synthetic gums, cellulose derivatives other than those listed above, carbohydrate-based substances such as acacia, gum tragacanth, locust bean gum, guar gum, agar, pectin, carageenin, soluble and insoluble alginates, carboxypolymethylene, casein, zein, and the like, and proteinaceous substances such as gelatin.

Within other embodiments of the invention, a sustained release delivery device or system is placed in the subject in proximity of the target of the active compound of Formula I, thus requiring only a fraction of the systemic dose (see, e.g., Goodson, in "Medical Applications of Controlled Release," supra, vol. 2, pp. 115-138, 1984; and Langer, 1990, Science 249:1527-1533, each incorporated herein by reference). In other embodiments, an oral sustained release pump may be used (see, e.g., Langer, supra; Sefton, 1987, CRC Crit. Ref. Biomed. Eng. 14:201; and Saudek et al., 1989, N. Engl. J. Med. 321:574, each incorporated herein by reference).

Pharmaceutical compositions and dosage forms comprising active compounds of Formula I may further include one or more carriers, excipients or additives, including, without limitation, binders, fillers, compression aides, lubricants, film-forming agents, glidants, anti-tacking agents, emulsifiers, suspending agents, flavors, flavor enhancers, sweeteners, flavorings, preservatives, buffers, wetting agents, disintegrants, effervescent agents and other conventional excipients and additives. Within exemplary embodiments, the compositions and dosage forms of the invention for treating acute pain, chronic pain, and/or symptoms of neuropathic disorders may include any one or combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to patients without causing deleterious side effects or interactions with the active agent.

In accordance with this invention, the compositions in the oral unit dosage forms comprising an active compound of Formula I will often contain a carrier. Suitable carriers include, for example, microcrystalline cellulose, lactose, sucrose, fructose, glucose dextrose, or other sugars, dibasic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol or mixtures thereof. In exemplary embodiments, the carrier dibasic calcium phosphate is employed. In other exemplary embodiments, a diluent or carrier is present in the composition in an amount of about 40% to 60% by weight of the composition.

Suitable lubricants include, for example, stearic acid, magnesium stearate, talc, calcium stearate, hydrogenated vegetable oils, sodium benzoate, sodium chloride, leucine carbowax, magnesium lauryl sulfate, colloidal silicon dioxide and glyceryl monostearate. Suitable glidants include, for example, colloidal silica, fumed silicon dioxide, silica, talc, fumed silica, gypsum and glyceryl monostearate. A variety of effervescent and disintegrant agents may be employed, which are well known in the art for their uses in the formulation of rapidly disintegrating tablets. By effervescent agent is meant a couple, typically an organic acid and a carbonate or bicarbonate.

Within exemplary embodiments of the invention, the pharmaceutical compositions and dosage forms comprise a unit oral dosage form, for example a capsule, lozenge, or tablet. Any conventional method of preparing pharmaceutical oral unit dosage forms can be utilized in preparing the unit dosage forms of this invention. In forming tablets, the composition will often be compressed by conventional means. The term "tablet" as used herein is intended to encompass powdered, compressed, granulated, microencapsulated, and all other pharmaceutical oral dosage formulations, of all sizes and shapes, whether coated or uncoated. These pharmaceutical oral unit dosage forms, will contain one or more of the conventional additional formulation ingredients noted above. In alternate embodiments, the oral dosage forms of the invention may contain any number of these additives and other ingredients (e.g., glidants, compression aides, disintegrants, lubricants, binders, flavors, flavor enhancers, sweeteners and preservatives), selected alone or in any combination for their known uses in preparing such dosage forms as tablets.

Additional compositions and methods of the invention comprise an active compound of Formula I formulated and administered in any of a variety of inhalation or nasal delivery forms known in the art. Devices capable of depositing aerosolized drug formulations in the sinus cavity or pulmonary alveoli of a patient include metered dose inhalers, nebulizers, dry powder generators, sprayers, and the like. Methods and compositions suitable for pulmonary delivery of drugs for systemic effect are well known in the art. Suitable formulations, wherein the carrier is often a liquid or gel, for administration, as for example, a nasal spray, nasal drops or a nasal gel, may include aqueous or oily solutions of an active compound of Formula I and any additional active or inactive ingredient(s) useful for nasal or pulmonary drug formulation. Intranasal and intrapulmonary delivery permits the passage of the active compound of Formula I to the blood stream directly after administering an effective amount of the compound to the nasal or pulmonary mucosal or alveolar surface. In addition, intranasal delivery can achieve direct, or enhanced, delivery of the active compound to the central nervous system (CNS). For intranasal and pulmonary administration, a liquid aerosol formulation will often contain an active compound of Formula I combined with a dispersing agent and/or a physiologically acceptable diluent. Alternative, dry powder aerosol formulations may contain a finely divided solid form of the active compound of Formula I and an optional dispersing agent allowing for the ready dispersal of the dry powder particles. With either liquid or dry powder aerosol formulations, the formulation will often be aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter, e.g., in a range of from about 2-5 microns, for nasal or pulmonary distribution to targeted mucosal or alveolar surfaces. These formulations may also include a sustained release vehicle, matrix, or binder for extended release of the active compound following administration, and may be provided in unit-dose or multi-dose containers, often containing or adapted for dispensing) a daily unit dose, or unit daily sub-dose, as described herein, or an appropriate fraction thereof, of the active compound. Other considerations include the construction of the delivery device, additional components in the formulation, and particle characteristics. These aspects of nasal or pulmonary administration of drugs are well known in the art, and optimization of these formulations, aerosolization means, and of delivery devices for effective administration of an active compound of Formula I is within the level of ordinary skill in the art.

Yet additional compositions and methods of the invention are provided for topical administration of an active compound of Formula I for the treatment of acute pain, chronic pain, and/or symptoms of a neuropathic disorder in mammals. Topical compositions may comprise an active compound of Formula I and any other active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may feature the active compound of Formula I dissolved or dispersed in a portion of water or other solvent or liquid to be incorporated in the topical composition or delivery device. Transdermal administration may be enhanced by the addition of a dermal penetration enhancer known to those skilled in the art. Alternatively, these formulations and devices may include a sustained release vehicle, matrix, or binder for extended release of the active compound following administration, and will be adapted to deliver a daily unit dose, or unit daily sub-dose, as described herein, or an appropriate fraction thereof, of the active compound. Formulations suitable for such topical dosage forms incorporate commonly utilized excipients, including means (e.g. a structure or matrix), for sustaining the absorption of drug over an extended period of time, for example up to 8, 12, 18, or 24 hours.

Yet additional compositions and dosage forms for administering an active compound of Formula I for treating acute pain, chronic pain, and/or a symptom of a neuropathic disorder in mammals are provided for parenteral administration, including aqueous and non-aqueous sterile injectable solutions which may optionally contain such know useful additives and other ingredients as anti-oxidants, buffers, bacteriostats, suspending agents, thickening agents, and/or solutes to render the formulation isotonic with the blood of the subject. These formulations may also include polymers and other sustained release vehicles, matrices, or binders for extended release following parenteral administration, and may be provided in unit-dose or multi-dose containers. Extemporaneous injection solutions, emulsions and suspensions may be prepared from sterile powders, granules and tablets of the kind previously described. Exemplary unit dosage formulations are those containing a daily unit dose, or unit daily sub-dose, as described herein, or an appropriate fraction thereof, of the active compound.

The pharmaceutical compositions and dosage forms of the current invention will typically be provided for administration in a sterile or readily sterilizable, biologically inert, and easily administered form.

Within exemplary embodiments of the invention, it has been found that the beneficial results for oral delivery of an active compound of Formula I are achieved through the use of hydrophilic slow release polymers, for example hydroxypropyl methyl cellulose. Within these exemplary embodiments, the hydrophilic polymer mediates relatively immediate onset of relief followed by continued maintenance of the active ingredient in the blood stream of the patient. The illustrative slow release polymer hydroxypropyl methyl cellulose used in accordance with this invention will often have a viscosity in the range of about 100 cps to about 100,000 cps, and in more detailed embodiments in the range of from about 15,000 cps to about 100,000 cps. On exposure to aqueous fluids such as in the body of the patient (e.g., when the oral dosage form such as a tablet is swallowed), these exemplary dosage forms become wet, and the polymer starts to hydrate to form a gel layer. The soluble nature of the active ingredient causes an initial burst from the external layer of the tablet. Thereafter an expansion of the gel layer occurs when water permeates into the tablet increasing the thickness of the gel layer. The soluble drug diffuses through the gel layer. Concomitantly, the outer layers become fully hydrated and dissolves, a process generally referred to as erosion. Water continues to permeate towards the tablet core until it has dissolved. This initial burst release of the active compound should be sufficient to provide a fast onset of action, often without the need for separate inclusion of an immediate release portion in the dosage form. This exemplary polymeric sustained release vehicle provides a release which constitutes an) initial burst followed by a continued sustained release of the active compound of formula I or its salt. In accordance with these exemplary embodiments, the composition containing the compound of formula I or its salt and a slow release polymer mediates release of the active compound so that not less than 10% of this active ingredient is released within 15 minutes and not less than 50% of this active ingredient is released within 4 hours a and not less than 85% by weight of this active ingredient is released within 12 hours. Other sustained release profiles as contemplated herein can be obtained using this and other sustained release polymers, or any other sustained release vehicle, matrix, binder, or coating as described herein.

For use within the methods and compositions of the instant invention, compounds of Formula I include the compound bicifadine, in pure form or in various mixtures, optical and geometric isomers of bicifadine, and all other compounds contemplated according to Formula I. In certain exemplary embodiments, the compositions and methods of the invention employ (±)-1-(4-methylphenyl)-3-azabicyclo[3.1.0]hexane hydrochloride (bicifadine HCl), enantiomers of bicifadine, pharmaceutically acceptable, active salts of bicifadine, prodrugs of bicifadine, polymorphs, hydrates, and solvates of bicifadine, or any combination of the foregoing forms of bicifadine. In more detailed embodiments, bicifadine hydrochloride is employed within therapeutic formulations, dosage forms, and methods of the invention.

Bicifadine HCl exists in at least two polymorphic crystalline forms, designated polymorph forms A and B (e.g., as described in U.S. patent application Ser. No. 10/702,397, corresponding to US Patent Publication 20040102638 A1, published May 27, 2004, incorporated herein by reference). Other polymorphic forms of bicifadine hydrochloride may exist and are likewise candidates for use within the methods and compositions of the invention for treating a neuropathic disorder and/or related symptom(s).

Polymorphs include compounds with identical chemical structure but different internal structures. Additionally, many pharmacologically active organic compounds regularly crystallize incorporating second, foreign molecules, especially solvent molecules, into the crystal structure of the principal pharmacologically active compound forming pseudopolymorphs. When the second molecule is a solvent molecule, the pseudopolymorphs can also be referred to as solvates. All of these additional forms of bicifadine are likewise useful within the methods and formulations of the invention.

Polymorph form A of bicifadine HCl can be formed, for example, by methods disclosed in U.S. Pat. No. 4,231,935 and U.S. Pat. No. 4,196,120 (each of which is incorporated herein by reference). Polymorph form B can be formed, for example, by methods disclosed in U.S. patent application Ser. No. 10/702,397, related international application PCT/US2003/035099 (Intl. Pub. No. WO04/043920), and priority U.S. Provisional Patent Application No. 60/424,982 (each incorporated by reference). For example, polymorph B can be formed from polymorph form A through the application of kinetic energy and through crystallization techniques. In one embodiment, kinetic energy in the form of agitating, stirring, grinding or milling can be applied to a pure composition of polymorph form A, or a mixture of forms A and B, particularly at selected temperatures, for example from about −200° C. to about 50° C., in another embodiment from about −200° C. to about 35° C., in a further embodiment from about −200° C. to about 0° C. In another embodiment, polymorph B can be crystallized from a solution of polymorph A that is heated and allowed to cool under defined conditions of temperature and time to form polymorph B. Under selected conditions, preparations of pure polymorph A of bicifadine, or mixtures of polymorph A and B of bicifadine, can be processed to yield desired compositions for use within the invention containing enriched quantities of polymorph B, for example ranging from approximately at least 10%, to about 10-20%, 20-35%, 35-50%, 50-70%, 70-85%, 85-95%, and up to 95-99% or greater (by weight) bicifadine polymorph B in the composition.

Polymorphs of bicifadine HCl may be characterized by their infrared spectra and/or their x-ray powder diffraction pattern. As described in U.S. patent application Ser. No. 10/702,397 incorporated above, X-ray powder diffraction (XRPD) analyses of polymorph forms A and B of racemic bicifadine hydrochloride were performed with a Shimadzu XRD-6000 X-ray powder diffractometer using Cu Kα radiation. The bicifadine was loaded onto the machine as a crystalline powder. The instrument was equipped with a fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-to theta continuous scan at 3/min (0.4 sec/0.02° step) from 2.5 to 40° 2θ was used. A silicon standard was analyzed to check the instrument alignment. Data were collected and analyzed using XRD-6000 v.4.1.

The X-ray powder diffraction pattern of polymorph form A of racemic bicifadine hydrochloride is given in terms of "d" spacing and relative intensities (I) is as follows (s=strong, m=medium, w=weak, v=very, d=diffuse) and these terms set forth in 1 below, and the X-ray powder diffraction pattern of form B of bicifadine hydrochloride is set forth in Table 2 below:

TABLE 1

Peak Positions, d-Spacings, and Intensities for Polymorph Form A Bicifadine Hydrochloride

| 2θ (deg) | d (Å) | $I^a$ |
|---|---|---|
| 5.35 | 16.50 | Vs |
| 10.61 | 8.33 | Vs |
| 11.45 | 7.72 | W |
| 15.22 | 5.82 | W |
| 15.93 | 5.56 | W |
| 16.97 | 5.22 | W |
| 18.37 | 4.83 | W |
| 20.04 | 4.43 | Md |
| 20.26 | 4.38 | Md |
| 21.22 | 4.18 | M |
| 21.89 | 4.06 | S |
| 23.12 | 3.84 | Md |
| 23.54 | 3.78 | Wd |
| 26.63 | 3.34 | M |
| 27.83 | 3.20 | Wd |
| 28.32 | 3.15 | Wd |
| 30.67 | 2.91 | Wd |
| 32.03 | 2.79 | S |
| 37.57 | 2.39 | W |
| 38.20 | 2.35 | W |

$^a$s = strong, m = medium, w = weak, v = very, d = diffuse

TABLE 2

Peak Positions, d-Spacings, and Intensities for Polymorph Form B Bicifadine Hydrochloride

| 2θ (deg) | d (Å) | $I^a$ |
|---|---|---|
| 5.08 | 17.39 | Vs |
| 10.07 | 8.77 | S |
| 15.19 | 5.83 | S |
| 16.83 | 5.27 | S |
| 18.64 | 4.76 | Md |
| 18.76 | 4.73 | Md |
| 19.64 | 4.52 | W |
| 20.16 | 4.40 | M |
| 21.96 | 4.05 | M |
| 22.37 | 3.97 | S |
| 23.16 | 3.84 | W |
| 24.00 | 3.70 | W |
| 25.27 | 3.52 | D |
| 27.33 | 3.26 | Md |
| 27.74 | 3.21 | M |
| 29.00 | 3.08 | M |
| 30.43 | 2.93 | Md |
| 31.84 | 2.80 | Wd |
| 32.29 | 2.77 | W |
| 35.27 | 2.54 | Wd |
| 35.64 | 2.52 | W |

$^a$s = strong, m = medium, w = weak, v = very, d = diffuse

Table 1 and Table 2 represent the XRPD pattern of the peak positions of bicifadine hydrochloride form A and form B, respectively. The results in these tables demonstrate the difference between the XRPD patterns of form A and form B. However, there are key peaks at given angles in this pattern which identify polymorph form B of bicifadine hydrochloride and are typically present in the XRPD pattern of polymorph form B irrespective of its particle size. These angles, expressed as 2θ (deg), locating these major peaks, which alone or in any distinguishing combination, distinguish bicifadine polymorph form B from form A, using Cu Kα radiation, are: 5.08; 10.07; 20.16; 25.17; and 30.43.

The infrared spectra were obtained for each of the samples using a Magna-IR 860® Fourier transform infrared (FT-IR) spectrophotometer (Thomas Nicolet) equipped with an Ever-Glo mid/far IR source, an extended range potassium bromide (KBr) beamsplitter, and a deuterated triglycine sulfate (DTGS) detector. The spectrophotometer measured the intensity of infrared light bands of each of the samples at given wavelengths. A diffuse reflectance accessory (the Collector™, Thermo Spectra-Tech) was used for sampling. Each spectrum represents 256 co-added scans collected from 400-4000 cm$^{-1}$ at a spectral resolution of 4 cm$^{-1}$. Sample preparation consisted of placing the sample of powder containing crystals in either polymorph form A or form B into a 13-mm diameter cup and leveling the material with a frosted glass slide. A background data set was acquired with an alignment mirror in place. The reflectance R is the ratio, at a given wavenumber, of the light intensity of the sample/light intensity of the background set. A Log 1/R(R=reflectance) spectrum acquired by taking a ratio of these two data sets (the sample and the background light intensities) against each other. The infrared spectrum of polymorph A or racemic bicifadine hydrochloride as a dry crystalline powder, as provided in Table 3, showed the indicated main peaks which characterized this polymorph. The infrared spectrum of polymorph B of racemic bicifadine hydrochloride in dry crystalline powder, as provided in Table 4, showed the indicated main peaks which characterize this polymorph.

TABLE 3

Infrared Peak Positions For Polymorph Form A
Bicifadine Hydrochloride.
All values in wavenumbers (cm$^{-1}$)

| |
|---|
| 3949 |
| 2923 |
| 2431 |
| 2280 |
| 2091 |
| 1895 |
| 1790 |
| 1595 |
| 1522 |
| 1430 |
| 1376 |
| 1233 |
| 1130 |
| 1088 |
| 1068 |
| 1050 |
| 900 |
| 825 |
| 781 |
| 714 |
| 689 |
| 652 |
| 574 |
| 533 |
| 437 |

TABLE 4

Infrared Peak Positions for Polymorph Form B
Bicifadine Hydrochloride.
All values in wavenumbers (cm$^{-1}$)

| |
|---|
| 3185 |
| 2769 |
| 2437 |
| 2276 |
| 2108 |
| 1908 |
| 1804 |
| 1658 |
| 1596 |
| 1518 |
| 1453 |
| 1403 |
| 1343 |
| 1305 |
| 1274 |
| 1209 |
| 1131 |
| 1111 |
| 1022 |
| 963 |
| 904 |
| 891 |
| 856 |
| 818 |
| 783 |
| 719 |
| 684 |
| 660 |
| 637 |
| 580 |
| 532 |
| 475 |
| 422 |

Table 3 and Table 4 provide the complete patterns of the infrared peak positions with respect to polymorph form A and polymorph form B of bicifadine hydrochloride respectively. However, there are certain key peaks, within this pattern, which are associated with polymorph form B of bicifadine hydrochloride and are sufficient to characterize this polymorph, individually or in any distinguishing combination. These peaks, expressed in wavenumbers (cm$^{-1}$), are: 2108; 891; 856; 719; and 660.

Bicifadine compositions for use within the invention may comprise any crystalline polymorphic or amorphous form of the compound, or mixture(s) thereof. In exemplary embodiments, effective therapeutic formulations and dosage forms will comprise substantially pure bicifadine HCl polymorph "form A" (i.e., having a concentration of about 95%-98% or greater by weight of total bicifadine present), substantially pure "form B", or any mixture of polymorph forms A and B. In certain embodiments, the formulation or dosage form of the invention may contain from about 10% to 98% polymorph form B. In other embodiments there may be present in the formulation or dosage form greater than about 50% polymorph form B, greater than about 75% polymorph B, greater than about 90% polymorph B, greater than about 98% polymorph B, or essentially pure polymorph B (i.e., where any levels of polymorph A, or any other form of bicifadine other than the B polymorph, that may be present are below a level of detection).

In additional embodiments, one or more isolated (+) or (−) enantiomers of bicifadine are employed within the methods and compositions of the invention. The (+) and (−) enantiomers of bicifadine, and methods for resolving these enantiomers to yield essentially pure compositions of the respective enantiomers, are reported by Epstein et al. (*J. Med. Chem.* 24(5):481, 1981; *NIDA Res. Monogr.* pp. 93-98, 1982). See, also U.S. Pat. No. 4,131,611; U.S. Pat. No. 4,118,417; U.S. Pat. No. 4,196,120; U.S. Pat. No. 4,231,935; and U.S. Pat. No. 4,435,419, each incorporated herein by reference). In exemplary embodiments, effective therapeutic dosage forms for treating mammalian subjects presenting with acute pain, chronic pain, or a neuropathic disorder will comprise essentially pure (+) bicifadine (i.e., having a concentration of 90-95% of the (+) enantiomer by weight of total bicifadine present), essentially pure (−) bicifadine, or any racemic mixture of the (+) and (−) enantiomeric forms of bicifadine. In certain embodiments, the formulation or dosage form may contain from about 10% to 98% (+) or (−) bicifadine. In other embodiments there may be present in the formulation or dosage form greater than about 50% (+) or (−) bicifadine, greater than about 75% (+) or (−) bicifadine, or greater than about 90% (+) or (−) bicifadine.

As noted above, in certain embodiments the methods and compositions of the invention employ pharmaceutically acceptable acid addition and/or base salts of a compound of Formula I. The term "pharmaceutically acceptable salts" refers to those salts of the parent compound which do not significantly adversely affect the pharmaceutical properties (e.g., toxicity, effectiveness, etc.) of the parent compound such as are conventionally used in the pharmaceutical art. Acid-addition salts may be prepared by treatment of the parent compound with the appropriate organic or inorganic acid in a manner well-known to those skilled in the art. It is to be understood that for the purposes of this invention, the acid-addition salts are equivalent to the parent free base.

Suitable acid addition salts are formed from acids, which form non-toxic salts. Examples include inorganic and organic acid addition salts, including but not limited to, hydrochloride, hydrobromide, hydroiodide, sulfate, hydrogen sulphate, nitrate, phosphate, hydrogen phosphate, citrate, fumarate, maleate, succinate, and pamoate salts. In other embodiments, useful pharmaceutically acceptable salts of compounds of Formula I include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; organic acid salts such as acetate, citrate, lactate, succinate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate, tartrate, gluconate and the like. Suitable base salts are formed from bases, which form non-toxic salts and examples are the aluminum, calcium, lithium, magnesium, potassium, sodium, zinc and diethanolamine salts.

In other detailed embodiments, the methods and compositions of the invention employ a prodrug of a compound of Formula I. Prodrugs are considered to be any covalently bonded carriers which release the active parent drug in vivo. Examples of prodrugs useful within the invention include esters or amides with hydroxyalkyl or aminoalkyl as a substituent, and these may be prepared by reacting such compounds as described above with anhydrides such as succinic anhydride.

The invention disclosed herein will also be understood to encompass methods and compositions using in vivo metabolic products of a compound of Formula I (either generated in vivo after administration of the subject precursor compound, or directly administered in the form of the metabolic product itself). Such products may result for example from the oxidation, reduction, hydrolysis, amidation, esterification and the like of the administered compound, primarily due to enzymatic processes. Accordingly, the invention includes methods and compositions of the invention employing compounds produced by a process comprising contacting a compound of Formula I with a mammalian subject (e.g., a mammalian cell, tissue, organ or individual) for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein will also be understood to encompass the methods and compositions of the invention employing a compound of Formula I isotopically-labelled by having one or more atoms replaced by an atom having a different atomic mass or mass number. Examples of isotopes that can be incorporated into the compounds of Formula I include isotopes of hydrogen, carbon, nitrogen, and oxygen, such as $^2$H, $^3$H, $^{13}$C, $^{14}$C, $^{15}$N, $^{18}$O, and $^{17}$O, respectively. Other useful labeling moieties in this context may include any detectable chemical moiety, for example conventional fluorophores, chemiluminescers, and enzymes.

Within related aspects of the invention, novel pharmaceutical compositions and unit dosage forms containing a compound of formula I, and methods for administering these compositions and dosage forms, are provided which are effective to alleviate or prevent acute pain, chronic pain, and/or pain or other symptoms associated with a neuropathic disorder in mammalian patients. The methods of the invention produce a strong, rapid onset of relief of targeted symptoms followed by a sustained maintenance of this relief for a long period of time.

Exemplifying compounds of Formula I, Bicifadine HCl, ((±)-1-(4-methylphenyl)-3-azabicyclo[3.1.0]hexane hydrochloride (also referred to as racemic 1-(p-toyl)-3-azabicyclo [3.1.0]hexane hydrochloride), is known as an effective, non-narcotic analgesic (see, e.g., U.S. Pat. Nos. 4,231,935; and 4,196,120, each incorporated herein by reference). Bicifadine HCl has been reported to be potent and active in the "Randall-Selitto" test, an animal model of acute inflammatory pain (see, e.g., Epstein et al., *J. Med. Chem.* 24(5):481, 1981; and Epstein et al., *NIDA Res. Monogr. pp.* 93-98, 1982, each incorporated herein by reference). Both opiates (e.g., morphine and codeine) and non-steroidal anti-inflammatory drugs (NSAIDs; e.g., aspirin) used to treat acute pain are also active in this model of acute, nociceptive pain. In addition, bicifadine has been reported to be as effective as codeine and tramadol, two commonly used analgesics for treating acute, nociceptive pain following dental surgery (Czobor P., et al., Stark J., Beer G., Petti S., Lippa A., Brown J., Beer B.: A Double-Blind, Placebo Controlled Randomized Study of DOV220,075 (bicifadine) SR and Codeine 60 mg in the Treatment of Post-Operative Dental Pain. *Presented at the 2nd Annual Scientific Meeting Mar.* 20-23, 2003 Chicago, Ill. *American Pain Society Abstract Database at http://www.ampainsoc.org/abstract/2003/data/index.html.* (Poster #915)); Czobor P., Stark J., Beer G., Brown J., Sunshine A., Konery S., Turpin M., Olson N., Otero A., Lippa A., Beer B.: A two center double-blind, placebo-controlled randomized study of DOV 220,075 (bicifadine) SR and Tramadol 100 mg in the treatment of post-operative dental pain. The Journal of Pain, 2004: 5(1), Supplement 1, p59. *Presented at the Joint APS and Canadian Pain Society Annual Meeting (23rd APS Annual Scientific Meeting) May* 6-9, 2004, Vancouver, BC Canada. *American Pain Society Abstract Database at http://www.ampainsoc.org/abstract/2004/data/index.html* (Poster #801); each incorporated herein by reference).

By employing the novel, sustained release compositions and dosage forms of the invention comprising an active compound of Formula I, including bicifadine, the invention provides effective tools and methods to treat and/or prevent acute pain in mammalian subjects. The pharmaceutical compositions and dosage forms of the invention effectively treat a wide variety of acute pain conditions and symptoms, including those associated with trauma and other injuries, for example burns; cuts; wounds; trauma; surgery; headaches; sprains; bone fractures; fibromyalgia; acute lower back pain; dorsopathy; dysmenorrhea; infection; dysfunction of the liver, pancreas, endocrine glands, kidney, bladder, gall bladder, spleen, hematopoetic system, vasculature or other body organ or tissue; torn or injured muscle, ligament, or tendon; acute exacerbation of a chronic or intermittent pain condition, including arthritic flare, migraine attack, and acute worsening of chronic lower back pain or chronic neuropathic pain. As used herein, the term "acute pain" will further be understood to encompass either an initial phase of a painful condition, which either largely resolves within several hours, days or months (typically lasting no more than about 3 months), or progresses on to a subacute pain (e.g., lasting 3-6 months) or chronic pain (e.g., persisting, in some cases intermittently, for more than 3 months, and often more than 6 months) condition. Acute pain also refers to a transient exacerbation or flare up of a chronic pain condition in which pain intensity worsens substantially, whereby supplemental treatment and/or upwards dose adjustment is indicated, provided that such treatment would be tolerated adequately.

The novel compositions and dosage forms of the invention comprising bicifadine or another active compound of Formula I also provide surprisingly effective tools and methods to treat and/or prevent chronic pain in mammalian subjects. The pharmaceutical compositions and dosage forms of the invention effectively treat a wide variety of chronic pain conditions and symptoms, including, for example; osteoarthritis pain; rheumatoid arthritis pain; cancer pain; and various other chronic pain conditions of non-neuropathic origin, including chronic low back pain, chronic lumbar and cervical pain, chronic fibromyalgia pain, chronic pain from arteriovenuous malformation, arachnoiditis, chronic pain from root avulsion, chronic postthoracotomy pain, and chronic postmastectomy pain of non-neuropathic origin.

Within a distinct embodiment of the invention, it has been surprisingly found that conditions and symptoms of chronic pain in mammalian subjects can be effectively treated by administering to the subject a therapeutically effective amount of an active therapeutic agent selected from a compound of Formula I, or a pharmaceutically acceptable salt, enantiomer, polymorph, solvate, hydrate, or prodrugs thereof, in a daily dosing regimen consisting of only one or two doses of the active agent per day. Based on findings from extensive studies employing bicifadine HCl for treating acute pain (for example acute dental pain and bunionectomy pain studies), exemplary unit doses (e.g., in the range of about 200 mg, 400 mg, or 600 mg) of bicifadine, yielding acceptable side effect levels, were found to have a period of analgesic efficacy for effectively treating acute pain of approximately 6 hours or even less. According to Czobor et al., supra, 2003, 2004, a duration of analgesic efficacy of bicifadine in acute dental pain studies was suggested using a distinct, "last observation carried forward" (LOCF) statistical method, and was projected to last up to 6 hours, or even up to 12 hours. However, these findings did not correlate directly to an actual period of analgesic efficacy of bicifadine for treating acute dental pain. On the contrary, the data relied upon by Czobor et al. to suggest a 6 hour or 12 hour efficacy period for bicifadine in acute pain studies were principally comprised of pain ratings assessed much earlier, at 1-4 hours post-dose. In contrast, actual periods of therapeutic efficacy of bicifadine for treating acute pain require direct assessment of pharmacokinetic and pain data throughout a full test period to reliably determine efficacy, and such determinations are further refined by analysis of rescue medication use by study subjects.

When these methods were applied to assess the duration of efficacy of bicifadine for treating acute pain, it was determined that patients administered bicifadine SR tablets in standard test dosage amounts (e.g., 200 mg, or 400 mg bicifadine SR tablets) did not show sustained, therapeutically-effective plasma levels of the drug for periods substantially longer than about six hours, or at most about eight hours (see, e.g., Stern et al., "Relationship Between Plasma Bicifadine Levels and Analgesic Effect in a Dental Pain Model, Abstract #314-P291 presented at the $11^{th}$ World Congress on Pain, Sydney, Australia, Aug. 21-26, 2005, incorporated herein by reference). As described in further detail in the Examples below, these findings correlated with a positive dose-dependent relationship for both the pharmacokinetics (AUC, Cmax) of bicifadine and the pharmacodynamic measures of efficacy of bicifadine for treating acute dental pain. Plasma bicifadine levels>1000 ng/ml were associated with the greatest pain relief, and drug levels between 500-1000 ng/ml were associated with significant analgesic efficacy. However, lower plasma drug levels of 500 ng/ml or less were not associated with significant analgesic effects. These data strongly indicated that effective treatment acute or chronic pain using a compound of Formula I would require at least three times daily. (tid) dosing, or four times daily (qid) dosing, to effectively treat subjects.

These conclusions are further substantiated by the use of rescue medication by subjects in the Stem et al. acute dental pain studies. Table 5 below summarizes information on the use of rescue medication for patients who took rescue medication among the various treatment groups in the clinical trial reported by Stern et al. (id.) A nonparametric analysis (Median Test) was conducted to evaluate the median latency to rescue medication. The Median Test showed that the difference among the five treatment groups (single dose of 200 mg, 400 mg or 600 mg bicifadine SR tablet, Tramadol 100 mg, or Placebo) did not reach statistical significance (Chi-square=4.7, df=4, P=0.32).

Survival analysis (Kaplan-Meier method, 95% confidence) was performed to compare the treatment groups with regard to time-to-rescue medication. For the purpose of this analysis, patients who did not take rescue medication until the end of the follow-up period were treated as censored observations. The analysis yielded a statistically significant difference among the treatment groups (Log-Rank test, Chi-square=26.9, df=4, P=0.0001). Subsequent pair-wise comparisons indicated that subjects receiving the bicifadine SR 400-mg (Log-Rank test, Chi-square=9.3, df=1, P=0.002), bicifadine SR 600-mg (Log-Rank test, Chi-square=12.4, df=1, P=0.0004), and tramadol 100-mg treatments (Log-Rank test, Chi-square=18.7, df=1, P=0.0001) were significantly less likely to use rescue medication than study subjects receiving placebo.

In view of the foregoing evidence, the present disclosure documenting efficacy of a reduced, bi-daily or less frequent dosing regimen of bicifadine to yield effective treatment of chronic pain are unexpected. The extended duration of treatment efficacy of preferred dosage amounts of bicifadine identified herein does not accord with the findings from the previously-published acute pain studies, nor with the pharmacokinetic data generated from these and related studies. It is a surprising benefit, therefore, that a dosing regimen consisting of only one or two doses of an active compound of Formula I effectively alleviates symptoms of chronic pain over an extended period. The extended period of efficacy of the novel compositions and dosage forms of the invention provide significant relief of chronic pain symptoms over a period of at least 8 hours, or at least 12 hours, often at least 18 hours, and up to 24 hours or longer.

The novel dosing methods of the invention for treating chronic pain are not limited to sustained release formulations of active compounds of Formula I. Rather, within this distinct aspect of the invention it is contemplated that all delivery modalities can be enlisted to achieve the unexpected therapeutic benefits identified herein attending a reduced dosing regimen for chronic pain. Thus, in certain embodiments, immediate release formulations of active compounds of Formula I may be employed within the subject dosing methods to achieve an unexpected duration of activity for alleviating symptoms of chronic pain.

Within these distinct aspects of the invention, methods for treating chronic pain comprising once daily or twice daily dosing of subjects will employ a once daily or twice daily effective amount of the active compound of Formula I, which will often be formulated for oral administration. Effective dosage amounts in this context will typically be between about 25 to 1800 mg, often between about 50 to 1200 mg, more often between about 75 to 1000 mg, or 100 to 600 mg, and in exemplary embodiments between about 200 to 400 mg, or 100 to 200 mg.

Although the novel methods of the invention providing effective treatments for chronic pain using bi-daily or less frequent dosing of a compound of Formula I are not dependent on use of the sustained release (SR) compositions and dosage forms described herein, it will often be advantageous to formulate the active therapeutic agent in such an SR dosage form using a sustained release vehicle, matrix, binder or coating material according to the teachings herein. Thus, in certain aspects of the invention, methods for treating chronic pain involving bi-daily or less frequent dosing of a compound of Formula I will employ a sustained release dosage forms as described herein, which in related embodiments will often yield desired results, e.g., by extending the release kinetics and lowering a side effect profile of the active therapeutic agent, as presently described.

Within exemplary embodiments, sustained release dosage forms useful for treating chronic pain on a once or twice daily dosing schedule will provide a mean maximum plasma concentration (Cmax) of the active therapeutic agent in a treatment subject which is less than about 80% of a Cmax provided in a control subject after administering the same amount of the active agent in an immediate release formulation. In related embodiments the sustained release dosage forms for treating chronic pain yield an Area Under the Curve (AUC) of the active therapeutic agent in a treatment subject which is less than about 80% of an AUC provided in a control subject administered the same amount of the active agent in an immediate release formulation. In additional related embodiments for treating chronic pain, a sustained release dosage form as contemplated herein will yields a Cmax and an AUC of the active therapeutic agent in a treatment subject which are each, respectively, less than about 80% of a Cmax and an AUC provided in a control subject following administration of the same amount of the active agent in an immediate release formulation.

In yet additional embodiments, sustained release dosage forms useful for treating chronic pain on a once or twice daily dosing schedule will exhibit an in vitro dissolution profile wherein about 5% to about 35% of the compound of Formula I is dissolved within 30 minutes, measured in a <711> dissolution test, Apparatus 1, USP 28, 2005, at 37.0° C.±0.5° C., using 900 ml 0.05M potassium phosphate monobasic buffer pH 6.8 and a basket or paddle speed of 75 rpm. In related embodiments, the sustained release dosage form will exhibit an in vitro dissolution profile wherein about 15% to about 40% of the compound of Formula I is dissolved within 1 hour according to the foregoing test parameters. In other related embodiments the sustained release dosage form will exhibit an in vitro dissolution profile wherein about 25% to about 60% of the compound of Formula I is dissolved within 2 hours according to these test parameters. In additional embodiments the sustained release dosage form will exhibit an in vitro dissolution profile wherein about 50% to about 80% of the compound of Formula I is dissolved within 4 hours. In yet additional embodiments the sustained release dosage form will exhibit an in vitro dissolution profile wherein about 70% to about 90-100% of the compound of Formula I is dissolved within 8 hours. In still other embodiments, the sustained release dosage form will exhibit an in vitro dissolution profile wherein about 75% to about 100% of the compound of Formula I is dissolved within 12 hours. In alternate embodiments, the sustained release dosage form will exhibit an in vitro dissolution profile wherein about 80% to about 100% of the compound of Formula I is dissolved within 24 hours. In this context, SR formulations which have a more extended dissolution profile will yield more extended in vivo release kinetics, such that extended in vivo release will provide effective therapeutic levels achieved by only once daily dosing that is sustained for a period of at least about 18 hours, and up to 24 hours, or longer. Exemplary formulations in this context include the long term sustained release formulations described below in Examples 2 and 3. The dissolution profiles/parameters of sustained release compositions and dosage forms of a compound of Formula I can be obtained or adjusted for any of the sustained release formulations and methods contemplated herein, including all contemplated compositions, dosage forms and treatment methods for acute pain, chronic pain and neuropathic disorders.

In more detailed embodiments of the invention for treating chronic pain using a once daily or twice daily dosing regimen, where a sustained release dosage form is selected, the sustained release vehicle, matrix, binder, or coating material, will often comprise a sustained release polymer. Exemplary sustained release polymers in this context include, but are not limited to, ethylcellulose, hydroxyethyl cellulose; hydroxyethylmethyl cellulose; hydroxypropyl cellulose; hydroxypropylmethyl cellulose; hydroxypropylmethyl cellulose phthalate; hydroxypropylmethylcellulose acetate succinate; hydroxypropylmethylcellulose acetate phthalate; sodium carboxymethylcellulose; cellulose acetate phthalate; cellulose acetate trimellitate; polyoxyethylene stearates; polyvinyl pyrrolidone; polyvinyl alcohol; copolymers of polyvinyl pyrrolidone and polyvinyl alcohol; polymethacrylate copolymers; and mixtures thereof.

Within additional embodiments of the invention, sustained release pharmaceutical compositions, dosage forms, and methods are provided that effectively treat and/or prevent neuropathic pain and related symptoms associated with neuropathic disorders in mammalian patients. Neuropathies and related symptoms attendant to neuropathic disorders include, but are not limited to, paraesthesias, allodynia, hyperalgesia and other sensory symptoms of neuropathies often referred to as "neuropathic pain", in mammals. Conventional analgesics, including NSAIDs and opiates, which are effective for treating general nociceptive pain, are rarely effective for neuropathic pain (*The Lancet,* 353:1959-1966, 1999). For example, morphine has a strong analgesic effect on nociceptive pain, but does not exhibit remarkable/sufficient activity for alleviating neuropathic pain. In fact, resistance to morphine therapy will provide a useful diagnostic index to differentiate subjects with neuropathy-associated pain amenable to treatment using the methods and compositions of the invention (see, e.g., Crosby et al., *J. Pain Symptom Manage*. 19(1):35-9, 2000; Chen et al., *J. Neurophysiol.* 87:2726-2733, 2002; Shir et al., *Harefuah* 118(8):452-4, 1990, each incorporated herein by reference). Accordingly, in certain aspects of the invention the compositions and methods herein are directed toward treatment of symptoms of a neuropathic disorder in individuals whose pain symptoms are insufficiently relieved by opioid treatment, and/or to treatment using other classes of analgesic drugs effective for treating nociceptive pain, such as NSAIDs. In this context, patients presenting with neuropathic disorders who will be amenable for treatment using the compositions and methods of the invention will often show less than a 50% reduction in the severity or frequency of their pain symptoms following administration of a nociceptive pain therapeutic agent (e.g., an opiate or NSAID) compared to placebo-treated or other suitable control subjects. In certain cases, the subject patients will show less than a 30%, 20%, or 10% reduction, or no measurable reduction, in the severity or frequency of pain symptoms after receiving the nociceptive pain drug, compared to control subjects exhibiting similar pain symptoms.

The compositions, dosage forms and methods effectively treat or prevent a wide variety of symptoms and conditions associated with neuropathies, including, for example, neuropathic pain and related symptoms associated with diabetic neuropathy; peripheral neuropathy; distal symmetrical polyneuropathy; post-herpetic neuralgia; trigeminal neuralgia; alcoholism-related neuropathy; HIV sensory neuropathy; sciatica; spinal cord injury; post-stroke neuropathy; multiple sclerosis; Parkinson's disease; idiopathic or post-traumatic neuropathy; mononeuritis; cancer-associated neuropathy; peripheral nerve trauma; nerve transection; carpal tunnel injury; neuropathy associated with Fabry's disease; vasculitic neuropathy; neuropathy associated with Guillain-Barre syndrome; entrapment neuropathy; phantom limb syndrome; and various additional neuropathic conditions that may be associated with, e.g., fibromyalgia, Wallenberg's syndrome, connective tissue disease, plexus irradiation, ischemic irradiation, hematomyelia, dyscraphism, tumor compression, arteriovenuous malformation, syphilitic myelitis, commissural myelotomy, arachnoiditis, root avulsion, certain chronic lower back pain syndromes of neuropathic origin, and reflex sympathic dystrophy.

The methods of the invention for treating acute pain, chronic pain, and/or neuropathic pain in mammalian subjects collectively comprise administering to a treatment subject a sustained release pharmaceutical composition or dosage form comprising a therapeutically effective amount (for a selected, acute pain, chronic pain, and/or neuropathic pain indication) of an active therapeutic agent comprising an active compound of Formula I (e.g., selected from bicifadine and pharmaceutically acceptable salts, enantiomers, polymorphs, solvates, hydrates, and prodrugs of bicifadine, and combinations thereof) combined with a sustained release vehicle, matrix, binder, or coating, as described herein. Following administration of the pharmaceutical composition or dosage form to the treatment subject, the active compound is released into the subject (e.g., into a gastrointestinal tract of the subject) and allowed to transit to a target site for delivery (e.g., a blood plasma or other tissue or compartment in the subject). In certain embodiments of the invention, this method results in a mean maximum plasma concentration (Cmax) of the active compound in the treatment subject which is less than about 80% of a Cmax obtained in a control subject after administration of the same amount of the active compound in an immediate release formulation. In other embodiments, the method results in an Area Under the Curve (AUC) of the active compound in the treatment subject which is less than about 80% of an AUC obtained in a control subject after administration of the same amount of the active compound in an immediate release formulation. In other embodiments, the method results in a Cmax and an AUC of the active compound in the treatment subject which are each, respectively, less than about 80% of a Cmax and an AUC obtained in a control subject after administration of the same amount of the active agent in an immediate release formulation.

According to these methods of the invention, targeted conditions or symptoms of acute pain, chronic pain, and/or a neuropathic disorder are substantially alleviated or prevented in the treatment subject, without attendant, unacceptable adverse side effects. Typically, subjects treated using the pharmaceutical compositions and dosage forms of the invention will exhibit an occurrence and/or severity of one or more targeted conditions or symptoms of acute pain, chronic pain, and/or a neuropathic disorder that is reduced by at least 10%, 20%, 30%, 50% or greater, up to a 75-90%, and even 95% or greater, compared to the occurrence and/or severity of the same one or more side effect(s) observed in placebo-treated control subjects under otherwise equivalent or comparable conditions.

Various animal and human models, assays and scoring systems are widely known in the art for determining therapeutic efficacy of the compositions, dosage forms and methods of the invention for treating conditions or symptoms of acute pain. As noted above, the analgesic efficacy of bicifadine HCl for treating acute pain has been previously established in animal models, for example in the "Randall-Selitto" test, an animal model of acute inflammatory pain (see, e.g., Epstein et al., *J. Med. Chem.* 24(5):481, 1981; and Epstein et al., *NIDA Res. Monogr.* pp. 93-98, 1982).

For determining therapeutic efficacy of the compositions, dosage forms and methods of the invention for treating conditions or symptoms of acute and/or chronic pain in human subjects, there is a variety of useful pain assessment models, assays and scoring systems known in the art. Exemplary methods and tools for assessing efficacy of compositions and methods of the invention for treating acute pain and/or chronic low back pain include the Pain Severity Rating (PSR), test; the Short-Form McGill Pain Questionnaire (SF-MPQ); and the Roland-Morris Disability Questionnaire. An exemplary PSR test uses a 100 mm visual analogue scale (VAS) to provide a patient pain severity rating, wherein patients are instructed to draw a vertical line on the scale to indicate the amount of low back pain they have experienced over the past 48 hours, from "no pain" to "worst pain imaginable". Study professionals measure the distance in mm (0-100) from the left side of the scale to the patient's vertical mark and record this number as the PSR value. The SF-MPQ rates the intensity of 15 sensory and affective components of pain and includes VAS and categorical scales to rate present overall pain intensity (see, e.g., Melzack R. The short-form McGill Pain Questionnaire. Pain 30:191-197, 1987). The SF-36 Health Survey is a generic quality of life instrument which has 36 items covering eight domains: physical functioning, role-physical, bodily pain, general health, vitality, social functioning, role-emotional, and mental health (see, e.g., Ware J E, Snow K K, Kosinski M, Gandek B. SF-36® Health Survey Manual and Interpretation Guide. Boston, Mass.: New England Medical Center, The Health Institute, 1993). For additional pain assessment methods and tools useful for determining efficacy of the compositions, dosage forms and methods of the invention, see, e.g., Strand et al., *Back Performance Scale for the assessment of mobility-related activities in people with back pain. Phys Ther.* 82:1213-

1223, 2002; Linton et al., *Int. J. Beh. Med.* 7(4):291-304, 2000; and Hsieh et al., *J. Manipulative Physiol. Ther.* 15(1): 4-9, 1992 (each incorporated herein by reference). Using such methods, the efficacy of bicifadine for treating acute pain has been demonstrated in human clinical trials to assess efficacy of bicifadine for treating acute, nociceptive pain following dental surgery—including trials testing activity of bicifadine HCl in side-by-side comparisons against, for example, opiates (see, e.g., Czobor P., et al., supra, 2003; Czobor P., et al., supra, 2004; and U.S. Pat. Nos. 4,231,935 and 4,196,120, each incorporated herein by reference).

In certain embodiments of the invention, subjects treated effectively using the methods and compositions described herein will exhibit an improvement, decreased occurrence, remission, or enhancement in a functional or activity-based, disability or quality of life measure or score associated with a targeted condition or symptom of acute pain, chronic pain, and/or a neuropathic disorder. In exemplary embodiments, one or more functional indices of impairment, or disability measures, in treated patients will be reduced by at least 10%, 20%, 30%, 50% or greater, up to a 75-90%, and even 95% or greater, compared to the occurrence and/or severity of the same one or more functional indices of impairment, or disability measures, in placebo-treated control subjects under otherwise equivalent or comparable conditions. For example, patients treated for acute pain, chronic pain, and/or a neuropathic disorder who exhibit a "baseline" functional disability index or score prior to treatment will exhibit an improvement (in terms of increased function, decreased disability, improved activity and/or other functional/quality of life measures) of at least 10%, 20%, 30%, 50% or greater, up to a 75-90%, and even 95% or greater improvement in the subject disability index or score. In more detailed embodiments, patients treated according to the methods and compositions of the invention will show at least a 10%, 20%, 30%, 50% or greater, up to a 75-90%, and even 95% or greater, improvement in a disability rating based on functional/activity measures, for example as embodied in the well-known Roland-Morris Disability Questionnaire, and/or SF-36 Health Survey. Any one or more disability indices may be reduced (corresponding to one or more enhanced functional/activity measures) in different patient populations or using different formulations or treatment protocols according to the) invention. Typically, multiple disability indices will be reduced, corresponding to enhancement of one or more functional/activity measures, in treated patients. In illustrative embodiments, subjects treated for acute pain, chronic pain, and/or a neuropathic disorder according to the methods and compositions of the invention will exhibit an improvement or decreased occurrence of one or more disability indices, corresponding to enhancement or reversal of one or more functional/activity measures, by at least 10%, 20%, 30%, 50% or greater, up to a 75-90%, and even 95% or greater, identified in the Roland-Morris Disability Questionnaire (RDQ) compared to the occurrence and/or severity of the same one or more functional indices of impairment, or disability measures, in placebo-treated control subjects under otherwise equivalent or comparable conditions. In certain embodiments, improvement in a comprehensive disability or functional/activity measure (e.g., an overall RDQ score) will be observed, for example a 10%, 20%, 30%, 50% or greater, up to a 75-90%, and even 95% or greater reduction in an RDQ score based on the following RDQ format.

Roland-Morris Disability Questionnaire

Because of My Back Pain Today: (Mark each numbered item YES or NO)

1. I stay at home most the time because of my back.
2. I change position frequently to try to get my back comfortable.
3. I walk more slowly than usual because of my back.
4. Because of my back, I am not doing any of the jobs that I usually do around the house.
5. Because of my back, I use a handrail to get upstairs.
6. Because of my back, I lie down to rest more often.
7. Because of my back, I have to hold on to something to get out of an easy chair.
8. Because of my back, I try to get other people to do things for me.
9. I get dressed more slowly that usual because of my back.
10. I only stand up for short periods of time because of my back.
11. Because of my back, I try not to bend or kneel down.
12. I find it difficult to get out of a chair because of my back.
13. My back is painful almost all the time.
14. I find it difficult to turn over in bed because of my back.
15. My appetite is not very good because of my back pain.
16. I have trouble putting on my socks (or stockings) because of the pain in my back.
17. I only walk short distances because of my back pain.
18. I sleep less well because of my back.
19. Because of my back pain, I get dressed with help from someone else.
20. I sit down for most the day because of my back.
21. I avoid heavy jobs around the house because of my back.
22. Because of my back pain, 1 am more irritable and bad tempered with people than usual.
23. Because of my back, I go upstairs more slowly than usual.
24. I stay in bed most of the time because of my back.

The foregoing methods and compositions of the invention that treat subjects with acute, chronic, and/or neuropathic pain by eliciting an improvement in, or reduced occurrence of, one or more disability indices, or by enhancing one or more functional/activity measures, may yield a corresponding decrease in pain symptoms in treated patients, but they may alternatively achieve the indicated therapeutic benefit indirectly without a direct, or at least directly proportionate, effect of alleviating pain in treated subjects. Thus, the subject methods and compositions may or may not correlate directly, or in all subjects, with a commensurate therapeutic benefit expressed in terms of reduced pain symptoms (e.g., as evinced by VAS or SF-MPQ scores).

For determining therapeutic efficacy of the compositions, dosage forms and methods of the invention for treating pain conditions and other symptoms of neuropathic disorders, there are also several useful animal and human models, assays and scoring systems known in the art. In this context, bicifadine HCl has now been tested and demonstrated to be effective in the spinal nerve ligation (Chung) model (see, e.g., Bennett, G. J., Chung, J. M., Honore, M., and Seltzer, Z. "Models of Neuropathic Pain. In: Current Protocols in Neuroscience" (J. N. Crawley, C. R. Gerfen, M. A. Rogawski, D. R. Sibley, P. Skolnick, and S. Wray, eds.) pp. 9.14.1-9.14.16. John Wiley & Sons, New York (2003); Morrow, T. J. "Animal Models of Painful Diabetic Neuropathy: The STZ rat model." In: Current Protocols in Neuroscience (J. N. Crawley, C. R. Gerfen, M. A. Rogawski, D. R. Sibley, P. Skolnick, and S. Wray, eds.) pp. 9.18.1-9.18.11. John Wiley & Sons, New York (2004), each incorporated herein by reference). These findings based on widely accepted models of neuropathic pain (i.e., the spinal nerve ligation model and STZ diabetes induced model), using well accepted endpoints modeling the symptoms associated with neuropathy, including thermal and mechanical-hyperalgesia, comprise the first report of efficacy for bicifadine in the treatment of neuropathic pain and other conditions and symptoms associated with neuropathic disorders (see, U.S. Provisional Patent Application No. 60/702,800, entitled Methods and Compositions For The Treatment of Neuropathies and Related Disorders, filed Jul. 26, 2005, incorporated herein by reference).

Surprisingly, the novel compositions, dosage forms and methods of the invention employing an active compound of Formula I effectively treat targeted symptoms of acute pain, chronic pain, and neuropathic pain and other symptoms associated with neuropathies, with a satisfactorily rapid onset of relief and over an extended period of time, without eliciting unacceptable, adverse side effects in subjects receiving the treatment. More specifically, the sustained release compositions and dosage forms of the invention for delivering active compounds of Formula I unexpectedly yield a significant reduction in one or more adverse side effects associated with delivery of the active compound in an "immediate release" formulation in a comparable dose. In more detailed embodiments, the compositions, dosage forms and methods of the invention yield effective treatment and/or prevention of acute pain, chronic pain, and/or neuropathy symptoms in a treatment subject, while exhibiting a significant reduction in the occurrence and/or severity of one or more adverse side effect(s) selected from euphoria, sedation, dizziness, headache, mydriasis, drowsiness, sleep impairment, disorientation, memory loss or other cognitive impairment, mood disorders, respiratory impairment, loss of motor function, nausea, constipation, dry mouth, low blood pressure, weight gain, eruption, dyspepsia, problems with cardiac function, dependence and/or withdrawal in the treatment subject—as compared to the occurrence and/or severity of the same one or more side effect(s) observed in control subjects over a similar time period following administration of the same amount of the active compound in an immediate release formulation.

Typically, subjects treated using the pharmaceutical compositions and dosage forms of the invention will exhibit an occurrence and/or severity of one or more of the foregoing adverse side effect(s) that is reduced by at least 10%, 20%, 30%, 50% or greater, up to a 75-90%, and even 95% or greater, compared to the occurrence and/or severity of the same one or more side effect(s) observed in control subjects receiving the same or comparable dose of the active compound of Formula I in an immediate release formulation under otherwise equivalent or comparable conditions. Within exemplary embodiments, the occurrence and/or severity of one or more adverse side effects selected from euphoria; dizziness; headache; mydriasis; sleepiness; drowsiness; and nausea in treatment subjects will be reduced by at least 10%, 20%, 30%, 50%, 75% or greater compared to the occurrence and/or severity of the same one or more side effect(s) observed in control subjects.

In a related aspect, the invention comprises a method of reducing one or more side effects that attend administration of an oral dosage form of a compound of Formula I. Within these methods, the compound of Formula I is provided in a sustained release oral dosage form and the dosage form is introduced into a gastrointestinal tract of a mammalian subject presenting with acute pain, chronic pain, or a neuropathic disorder. The method further includes releasing the active compound of Formula I in a sustained release (i.e., sustained release, delayed release, slow release, extended release, gradual release, controlled release, modified release, or pulsatile release) delivery mode into the gastrointestinal tract (e.g., the intestinal lumen) of the subject over a period of hours, during which the active compound reaches, and is sustained at, a therapeutic concentration in a blood plasma, tissue, organ or other target site of activity (e.g., a central nervous system (CNS) tissue, fluid or compartment) in the subject. When following this method, the side effect profile of the active compound is less than a side effect profile of an equivalent dose of the active compound administered in an immediate release oral dosage form. In more detailed embodiments, subjects treated using the methods of the invention for reducing side effects associated with administration of an oral dosage form of a compound of Formula I will exhibit an occurrence and/or severity of one or more of the foregoing adverse side effect(s) that is reduced by at least 10%, 20%, 30%, 50% or greater, up to a 75-90%, and even 95% or greater, compared to the occurrence and/or severity of the same one or more side effect(s) observed in control subjects as described above. Within exemplary embodiments, the occurrence and/or severity of one or more adverse side effects selected from euphoria; dizziness; headache; mydriasis; sleepiness; drowsiness; and nausea in treatment subjects will be reduced by at least 10%, 20%, 30%, 50%, 75% or greater compared to the occurrence and/or severity of the same one or more side effect(s) observed in control subjects.

The compositions, dosage forms and methods of the invention for treating or preventing acute pain, chronic pain, and/or neuropathic disorders or related symptoms generally employ a therapeutically effective amount or dose of a compound of Formula I (including all active derivatives, enantiomers, salts, polymorphs, solvates, hydrates, and/or prodrugs of these compounds), optionally formulated with one or more additional components, such as physiologically-compatible carriers, additives, buffers, excipients, preservatives, and the like. The formulations, dosage forms and methods of the invention will be therapeutically effective and well tolerated among mammalian subjects, in useful and commercially feasible dosage amounts as indicated herein, and without unacceptable adverse side effects. As used herein, the terms "therapeutically effective amount" and "therapeutically effective dose" refer to effective amount or dose of an active compound of Formula I that is sufficient to elicit a desired pharmacological or therapeutic effect in a mammalian subject—typically resulting in a measurable reduction in an occurrence, frequency, or severity of acute pain, chronic pain, or symptom(s) associated with a neuropathic disorder in the subject. In certain embodiments, when a compound of the invention is administered to treat one of these indications, an effective amount of the compound will be an amount sufficient in vivo to delay or eliminate onset of one or more symptoms associated with the targeted indication. Therapeutically-effective amounts, formulations and dosages can alternatively be determined by an administered formulation/dosage that yields a decrease in the occurrence, frequency or severity of one or more symptoms of acute pain, chronic pain, or a neuropathic disorder. In other embodiments, a therapeutically-effective amount, formulation or dose will yield a detectable, therapeutic reduction in the nature or severity, occurrence, frequency, and/or duration of one or more symptom(s) associated with the targeted condition or disorder. Therapeutically effective amounts and dosage regimens will be readily determinable by those of ordinary skill in the art, often based on routine clinical or patient-specific factors.

In exemplary embodiments of the invention, the compound of formula I is administered in an effective unit dosage amount of from about 25 mg to about 600 mg. Within these exemplary embodiments, the compound of Formula I may be provided in a sustained release, unit oral dosage composition comprising about 40% to 60%, by weight of the composition, of a pharmaceutically acceptable carrier, and from about 15% to 50% by weight of the composition of a slow release matrix, such as polymeric slow release matrix (e.g., hydroxypropyl methyl cellulose), with the carrier and the active ingredient dispersed in the slow release matrix. In more detailed embodiments, these exemplary formulations and methods employ a unit dosage composition comprising about 20% to 25% by weight, based upon the total weight of the composition, of a slow release matrix, which produces a controlled release formulation of the active compound of formula I causing an initial rapid release of the active compound in the blood system of the patient to provide an immediate relief of pain and thereafter maintaining a relatively constant slow release of the active compound for an extended period. In accordance with these exemplary embodiments, the compound of formula I or its salts are administered in an effective amount to alleviate pain. In general oral dosages of from about 0.5 mg/kg to about 20 mg/kg per day are used. However the amount of the compound of formula I or its salt in the oral unit dose to be administered will depend to a large extent on the amount of pain and the weight of the patient and of course be subject to the physician's judgment. For example, for patients of from about 60 kg to about 80 kg unit oral dosage forms containing from about 100 mg to about 600 mg will often be utilized, with dosages of about 200 to 400 mg being generally preferred.

In other embodiments of the invention, suitable effective unit dosage amounts of the active compound of Formula I may range from about 1 to 1200 mg, 50 to 1000 mg, 75 to 900 mg, 100 to 800 mg, or 150 to 600 mg. In certain embodiments, the effective unit dosage will be selected within narrower ranges of, for example, 10 to 25 mg, 30 to 50 mg, 75 to 100 mg, 100 to 150 mg, 150 to 250 mg, 200-400 mg, 250 to 500 mg, or 400-600 mg. These and other effective unit dosage amounts may be administered in a single dose, or in the form of multiple daily, weekly or monthly doses, for example in a dosing regimen comprising from 1 to 5, or 2-3, doses administered per day, per week, or per month. In exemplary embodiments, dosages of 10 to 25 mg, 30 to 50 mg, 75 to 100 mg, 100 to 200 mg, or 250 to 500 mg, are administered one, two, three, or four times per day. In more detailed embodiments, dosages of 50-75 mg, 100-150 mg, 150-200 mg, 250-400 mg, or 400-600 mg are administered once daily, twice daily, or three times daily. In alternate embodiments, dosages are calculated based on body weight, and may be administered, for example, in amounts from about 0.5 mg/kg to about 30 mg/kg per day, 1 mg/kg to about 15 mg/kg per day, 1 mg/kg to about 10 mg/kg per day, 2 mg/kg to about 20 mg/kg per day, 2 mg/kg to about 10 mg/kg per day or 3 mg/kg to about 15 mg/kg per day.

The amount, timing and mode of delivery of the active compound of Formula I will be routinely adjusted on an individual basis, depending on such factors as weight, age, gender, and condition of the individual, symptom presentation pattern, whether the administration is prophylactic or therapeutic, and on the basis of other factors known to effect drug delivery, absorption, pharmacokinetics, including half-life, and efficacy. An effective dose or multi-dose treatment regimen for the compounds of the invention will ordinarily be selected to approximate a minimal dosing regimen that is necessary and sufficient to substantially prevent or alleviate the targeted pain condition or symptom(s) in the subject, as described herein.

Suitable routes of administration for the active compounds of Formula I to treat or prevent acute pain, chronic pain, or symptoms of a neuropathic disorder include, but are not limited to, oral, buccal, nasal, aerosol, topical, transdermal, mucosal, injectable, slow release, controlled release, although various other known delivery routes, devices and methods can likewise be employed.

Within additional aspects of the invention, combinatorial formulations and methods are provided which employ an active compound of Formula I and one or more additional active agents, that are combinatorially formulated or coordinately administered with the compound of Formula I. These combinatorial formulations and coordinate treatment methods employ an effective amount of an active compound of Formula I (including pharmaceutically effective enantiomers, salts, solvates, hydrates, polymorphs or prodrugs thereof), and one or more secondary or adjunctive active agent(s) that is/are combinatorially formulated or coordinately administered with the compound of Formula I. These combinatorial formulations and coordinate treatment methods are effective to modulate, alleviate, treat or prevent one or more symptom(s) of a targeted condition or symptom of acute pain, chronic pain, or a neuropathic disorder in a mammalian subject. Exemplary combinatorial formulations and coordinate treatment methods in this context employ an active compound of Formula I in combination with one or more known, secondary or adjunctive treatment agents effective for treating pain and/or symptoms of neuropathic disorders. Contemplated useful secondary or adjunctive therapeutic agents in this context include, but are not limited to, NSAIDs (e.g., aspirin and ibuprofen); COX-2 inhibitors; synthetic and natural opiates (e.g., oxycodone, meperidine, morphine, and codeine); mexiletine; baclofen; tramadol; antiarrhythmics; anticonvulsants (e.g., lamotrigine, gabapentin, valproic acid, topiramate, famotodine, phenobarbital, diphenylhydantoin, phenyloin, mephenyloin, ethotoin, mephobarbital, primidone, carbamazepine, ethosuximide, methsuximide, phensuximide, trimethadione, benzodiazepines such as diazepam, phenacemide, acetazolamide, progabide, clonazepam, divalproex sodium, magnesium sulfate injection, metharbital, paramethadione, phenyloin sodium, valproate sodium, clobazam, sulthiame, dilantin, diphenylan; capsaicin cream; membrane-stabilizing drugs (e.g., lidocaine); N-methyl-D-aspartate receptor (NMDA) antagonists such as ketamine; as well as all other known analgesic drugs and drugs useful for treating symptoms of neuropathies, such as pregabalin, harkoseride, amitriptiline, desipramine and other related tricyclic antidepressants.

To practice a coordinate treatment method of the invention, an active compound of Formula I is administered, simultaneously or sequentially, in a coordinate treatment protocol with one or more of the secondary or adjunctive therapeutic agents or methods described above. The coordinate administration may be done simultaneously or sequentially in either order, and there may be a time period while only one or both (or all) active therapeutic agents, individually and/or collectively, exert their biological activities. A distinguishing aspect of all such coordinate treatment methods is that the active compound of Formula I exerts at least some detectable therapeutic activity as described herein, and/or elicits a favorable clinical response, which may or may not be in conjunction with a secondary clinical response provided by the secondary or adjunctive therapeutic agent. Often, the coordinate administration of an active compound of Formula I with a secondary or adjunctive therapeutic agent as contemplated herein will yield an enhanced therapeutic response, and/or will yield a reduced side effect profile, compared to the therapeutic response and side effect profile elicited by either or both the compound of Formula I and secondary or adjunctive agent, alone.

The following examples illustrate certain embodiments of the present invention, and are not to be construed as limiting the present disclosure.

IN THE EXAMPLES

Bicifadine HCl is the hydrochloric acid salt of the compound of formula I.

Emcompress is the carrier dibasic calcium phosphate.

Methocel K100M is the hydrophilic polymeric hydroxypropyl methyl cellulose having a viscosity of 100,000 cps for a 2% solution in water [HPMC].

Methocel K100LV is the hydrophilic polymeric hydroxypropyl methyl cellulose having a viscosity of 100 cps for a 2% solution in water [HPMC].

Carbopol 971P is a polyacrylic acid polymer having a viscosity of 4,000 to 12,000 cps for a 0.5% solution at pH 7.5[PAA].

Aerosil 200 is colloidal silicon dioxide.

A vicel PH101 is microcrystalline cellulose.

The content of the active ingredient of formula I in the sample as reported in the dissolution tables was determined by HPLC.

Example 1

Preparation of 200 mg, Bicifadine HCl Tablet

A first example of a bicifadine HCl 200 mg sustained release (SR) tablet (referred to below as "formulation F" or "treatment F") was prepared using the following ingredients. In the table below the "% composition" is the % by weight of the ingredient based upon the total weight of the composition.

(i) Bicifadine HCl 200 mg SR Tablets
Batch Size: 5.2 kg

| Material | % Composition | Mg/tablet |
|---|---|---|
| Bicifadine HCl | 31.25 | 200.0 |
| Methocel K100M | 20.00 | 128.0 |
| Emcompress | 47.75 | 305.6 |
| Magnesium Stearate | 0.50 | 3.2 |
| Aerosil 200 | 0.50 | 3.2 |

The tablets were prepared from the above ingredients according to the procedure set forth below.

(1) Sieve the Bicifadine HCl through a 1 mm screen, and collect in a polyethylene lined container. Weigh the exact quantity required.

(2) Add the Aerosil 200 to a portion of the Emcompress. Bag blend for 2 minutes and pass through a 600 micron screen.

(3) Add the Magnesium Stearate to a portion of the Emcompress. Bag blend for 2 minutes and pass through a 600 micron screen.

(4) Transfer the components to a V cone blender (Pharmatech Mobile Multi-Blend Blender, equipped with 25 L V cone), and blend for 20 minutes at 18 rpm.

Order of addition:
Half of Emcompress
Sieved Emcompress/Aerosil mix
Sieved Bicifadine HCl
Methocel K100M
Remaining Emcompress (5) Add the Sieved Emcompress I Magnesium Stearate mix, and blend for a further 3 minutes at 18 rpm.

(6) Tablet the blend using a rotary tablet press (Piccola Tablet Press)

Tabletting Parameters
Press Speed Setting: 6
Punch Description: 18×8 mm oval normal concave
No of punches: 5
Main Compression Force Setting: 2.5
Filomatic Speed Setting 4
Target Tablet Weight: 0.640 g (Range: 0.595-0.685 g)
Target Tablet Hardness 150N (Range: 105-195N)

Example 2

Preparation of 200 mg Bicifadine HCl SR tablet

A second example of a Bicifadine HCl 200 mg SR tablet (referred to herein below as "formulation B" or "treatment B") was prepared using the following ingredients. In the table below the "% composition" is the % by weight of the ingredient based upon the total weight of the composition.

| Material | % Composition | Mg/tablet |
|---|---|---|
| Bicifadine HCl | 31.25 | 200.0 |
| Methocel K100M | 40.00 | 256.0 |
| Emcompress | 27.25 | 174.4 |
| Magnesium Stearate | 01.00 | 006.4 |
| Aerosil 200 | 00.50 | 003.2 |

These Bicifadine HCl SR tablets were manufactured similarly to those in Example 1.

Example 3

Preparation of 200 mg Bicifadine HCl SR Tablet

A third example of bicifadine HCl 200 mg SR tablet (referred to herein below as "formulation C" or "treatment C") was prepared using the following ingredients. In the table below the "% composition" is the % by weight of the ingredient based upon the total weight of the composition.

| Material | % Composition | Mg/tablet |
|---|---|---|
| Bicifadine HCl | 31.25 | 200.0 |
| Methocel K100M | 60.00 | 384.0 |
| Emcompress | 07.25 | 046.4 |
| Aerosil 200 | 00.50 | 003.2 |
| Magnesium Stearate | 01.00 | 006.4 |

These Bicifadine HCl SR tablets were manufactured similarly to those of Example 1.

Example 4

Dissolution of 200 mg Bicifadine HCl Tablets

Dissolution Testing of the bicifadine SR tablets from examples 1, 2 and 3 (formulations F, B, and C, respectively) was performed using USP 1 Apparatus, 20 mesh baskets, 75 rpm, 900 ml phosphate buffer pH 6.8±0.05, 37° C.±0.5° C.

| Time (Hrs.) | Formula F (Ex. 1) | Formula B (Ex. 2) | Formula C (Ex. 3) |
|---|---|---|---|
| 0.25 | 14.6 | 11.2 | 9.2 |
| 0.5 | 22.9 | 16.8 | 13.1 |
| 1 | 33.5 | 24.0 | 21.1 |
| 2 | 48.4 | 37.3 | 33.2 |
| 4 | 69.1 | 54.4 | 48.4 |
| 8 | 89.7 | 76.8 | 69.7 |

-continued

| Time (Hrs.) | Formula F (Ex. 1) | Formula B (Ex. 2) | Formula C (Ex. 3) |
|---|---|---|---|
| 12 | 99.9 | 88.4 | 82.7 |
| 22 | — | 100.6 | 95.5 |

For these SR tablets, a substantial amount of the active ingredient is released at the early timepoints. For formulation F, for example, a significant portion of the total amount of active ingredient (approximately 15%) is released within the first 15 minutes, with the remainder released in a slow and continuous manner over the remaining 12 hrs.

Example 5

Preparation of 200 mg Bicifadine SR HCl Tablet

A fourth example of a bicifadine HCl 200 mg SR tablet was prepared using the following ingredients. In the table below the "% composition" is the % by weight of the ingredient based upon the total weight of the composition.

| Material | % Composition | Mg/tablet |
|---|---|---|
| Bicifadine HCl | 31.25 | 200.00 |
| Methocel K100M | 30.00 | 192.00 |
| Emcompress | 37.75 | 241.60 |
| Aerosil 200 | 00.50 | 003.20 |
| Magnesium Stearate | 00.50 | 003.20 |

These Bicifadine HCl SR tablets were manufactured similarly to those in Example 1.

Example 6

Preparation of 200 mg SR Bicifadine HCl Tablet

A fifth example of a bicifadine HCl 200 mg SR tablet was prepared using the following ingredients. In the table below the "% composition" is the % by weight of the ingredient based upon the total weight of the composition.

| Material | % Composition | Mg/tablet |
|---|---|---|
| Bicifadine HCl | 31.25 | 200.00 |
| Methocel K100M | 13.60 | 087.04 |
| Methocel K100LV | 26.40 | 168.96 |
| Emcompress | 27.75 | 177.60 |
| Aerosil 200 | 00.50 | 003.20 |
| Magnesium Stearate | 00.50 | 003.20 |

These Bicifadine HCl SR tablets were manufactured similarly to those in Example 1.

Example 7

Dissolution of 200 mg SR Bicifadine HCl Tablets

Dissolution Testing of the bicifadine tablets produced in Examples 5 and 6 was performed using USP 1 Apparatus, 20 mesh baskets, 75 rpm, 900 ml phosphate buffer pH 6.8±0.05, 37° C.±0.5° C.

| Time (Hrs) | Example 5 | Example 6 |
|---|---|---|
| | Mean % Released | |
| 0.25 | 13.9 | 13.3 |
| 0.5 | 21.6 | 19.2 |
| 1 | 28.3 | 27.7 |
| 2 | 41.8 | 41.4 |
| 4 | 60.7 | 60.4 |
| 8 | 85.3 | 85.5 |
| 12 | 96.1 | 97.4 |
| 22 | 104.1 | 101.0 |

Example 8

Preparation of 180 mg Bicifadine HCl SR Tablet

Additional exemplary bicifadine HCl (180 mg) SR tablets were prepared according to the following table ("% composition" is the % by weight of the ingredient based upon the total weight of the composition).

| Material | G | H | I | J | K | L |
|---|---|---|---|---|---|---|
| | % Composition | | | | | |
| Bicifadine HCl | 30.0 | 30.0 | 30.0 | 30.0 | 40.0 | 40.0 |
| Methocel K100M | 30.0 | — | 30.0 | — | 30.0 | 40.0 |
| Methocel K15M | — | 30.0 | — | 30.0 | — | — |
| Emcompress | — | — | 38.5 | 38.5 | — | — |
| Pharmatose DCL 11 | 38.5 | 38.5 | — | — | — | — |
| Mannitol | — | — | — | — | 23.5 | 18.5 |
| Aerosil 200 | 00.5 | 00.5 | 00.5 | 00.5 | 00.5 | 00.5 |
| Magnesium Stearate | 01.0 | 01.0 | 01.0 | 01.0 | 01.0 | 01.0 |
| Tablet Weight | 600 mg | 600 mg | 600 mg | 600 mg | 450 mg | 450 mg |

These blends were manufactured using manual blending. The tablets were compressed manually using 300 bar pressure and an Enerpac single station tablet press using 13 mm normal concave tooling.

Example 9

Dissolution of 180 mg Bicifadine HCl SR Tablets

Dissolution Testing of the exemplary bicifadine SR tablets produced in Example 8 was performed using USP 2 Apparatus, 50 rpm, 900 ml phosphate buffer pH 6.8±0.05, 37° C.±0.5° C.

| Time (Hrs) | G | H | I | J | K | L |
|---|---|---|---|---|---|---|
| | Mean % Released | | | | | |
| 0.25 | 17.7 | 17.2 | 16.8 | 21.0 | 18.9 | 17.8 |
| 1 | 25.5 | 24.9 | 24.4 | 30.7 | 27.1 | 22.7 |
| 4 | 52.3 | 51.0 | 48.7 | 57.4 | 54.1 | 54.3 |
| 8 | 74.3 | 70.3 | 66.0 | 73.2 | 74.3 | 75.0 |
| 12 | 88.6 | 84.4 | 77.2 | 84.1 | 87.8 | 89.0 |
| 22 | 101.4 | 99.3 | 91.1 | 96.5 | 99.8 | 100.8 |

Example 10

Preparation of 200 mg Bicifadine HCl SR Tablet

This example is directed to the preparation of 200 mg Bicifadine HCl SR tablets which contain another exemplary slow release component, such as a polyacrylic acid polymer alone (formulation D), or polyacrylic acid polymer combined with hydroxypropylmethyl cellulose (formulation E).

These bicifadine HCl 200 mg SR tablets were prepared using the following ingredients. In the table below, the "% composition" is the % by weight of the ingredient based upon the total weight of the composition.

|  | Formula D | | Formula E | |
| --- | --- | --- | --- | --- |
| Material | % Composition | Amount mg/tab | % Composition | Amount mg/tab |
| Bicifadine HCl | 31.25 | 200 | 31.25 | 200 |
| Carbopol 971P | 15.0 | 96 | 10.0 | 64 |
| Methocel K100M | — | — | 40.0 | 256 |
| Emcompress | 52.25 | 334.4 | 17.25 | 110.4 |
| Aerosil | 0.5 | 3.2 | 0.5 | 3.2 |
| Magnesium Stearate | 1.0 | 6.4 | 1.0 | 6.4 |

The Bicifadine HCl SR tablets were manufactured similarly to those in Example I, with Carbopol 971P substituting Methocel K100M as required. The target tablet hardness was 200N (Range: 140-260N).

Example 11

Dissolution of 200 mg Bicifadine HCl SR Tablets of Example 10

Dissolution Testing of the tablets produced in example 10 above was performed using USP 1 Apparatus, 20 mesh baskets, 75 rpm. The dissolution medium used was 900 ml 0.01N HCl for the first two hours, followed by 900 ml phosphate buffer pH 6.8±0.05, 37° C.±0.5° C. for the remaining time.

| Time (hrs) | Formula D | Formula E |
| --- | --- | --- |
|  | Mean % Released | |
| 0.25 | 17.6 | 12.0 |
| 0.5 | 23.6 | 16.7 |
| 1 | 31.2 | 22.9 |
| 2 | 42.9 | 32.8 |
| 4 | 49.9 | 42.9 |
| 8 | 59.7 | 58.1 |
| 12 | 65.7 | 67.4 |
| 22 | 74.2 | 81.2 |

Example 12

Preparation of 100 mg Bicifadine HCl IR Tablet

This example is directed to the preparation of exemplary bicifadine HCl 100 mg immediate release (IR) tablets (referred to herein below as "formulation A" or "treatment A") which do not contain any hydrophilic slow release polymer matrix. These bicifadine HCl 100 mg IR tablets were prepared using the following ingredients ("% composition" is the % by weight of the ingredient based upon the total weight of the composition).

| Material | % Composition | Mg/tab |
| --- | --- | --- |
| Bicifadine | 15.625 | 100 |
| Avicel PH1Ol | 72.875 | 466.4 |
| Polyplasdone | 10.0 | 64 |
| Aerosil | 0.5 | 6.4 |
| Magnesium Stearate | 1.0 | 3.2 |

The IR tablets were prepared from these ingredients as set forth below:
(1) Blend Avicel PH101 with Aerosil200 in a ratio of ca. 1:40 for two minutes, then pass through a screen of aperture 600Tm.
(2) Blend Avicel PH101 with Magnesium Stearate in a ratio of ca.1:20 for two minutes, then pass through a screen of aperture 600Tm.
(3) Pass Bicifadine raw material through a 1 mm screen. Weigh the exact amount required.
(4) Transfer the components to a V cone blender (Pharmatech Mobil Multi-Blend Blender),
Order with 25 L cone, and blend for ten minutes at 18 rpm
Approximately half of the remaining Avicel PH101
Polyplasdone
Screened Avicel/Aerosil blend to blender.
Remaining Avicel to the blender.
(5) Add the screened Avicel Magnesium Stearate to the blender and blend for three minutes at 18 rpm. Tablet the blend using a rotary tablet press (Piccola Tablet Press), using 18×8 mm oval normal concave tooling to a target tablet weight of 0.640 g (Range:0.595-0.685 g).

Example 13

Dissolution of 100 mg Bicifadine HCl IR Tablets of Example 12

Dissolution Testing of the exemplary IR bicifadine HCl tablets produced in Example 12 was performed using USP 1 Apparatus, 20 mesh baskets, 75 rpm. The dissolution medium used was 900 ml 0.01N HCl, 37° C.±0.5° C.

| Time (hrs) | Formulation A % Released |
| --- | --- |
| 0.083 | 95.6 |
| 0.5 | 101.1 |

Example 14

In Vivo Pharmacokinetic Study

This example demonstrates that the use of exemplary bicifadine sustained release (SR) oral dosage forms, e.g., having from about 20-50% by weight of hydroxypropylmethyl cellulose hydrophilic slow release polymer matrix produces a sustained maintenance of bicifadine in the blood for longer periods of time than utilizing comparable matrix systems which contain greater than 50% hydroxypropylmethyl cellulose as well as systems which contain other sustained release polymer matrixes. In addition, this example compares the various indicated SR bicifadine formulations against an exemplary Immediate Release (IR) bicifadine formulation.

In this study the following treatments were evaluated: 1) Treatment A=IR Tablets of Example 12; 2) Treatment B=SR Tablets of Example 2 (40% HPMC); 3) Treatment C=SR Tablets of Example 3 (60% HPMC); 4) Treatment D=SR Tablets of Example 10 (40% HPMC and 10% PAA); and 5) Treatment E=SR Tablets of Example 10 (PAA).

A five treatment, randomized balanced crossover study in 15 healthy volunteers examining the absorption of bicifadine HCl sustained release tablets relative to absorption of bicifadine HCl immediate release tablets was performed. Objectives of this study included:
   To evaluate the effect of different types/levels of matrix-forming polymers within bicifadine SR tablets.

To evaluate the release of bicifadine from exemplary SR and IR dosage forms.

To evaluate safety and tolerability of SR and IR bicifadine oral dosage forms.

Methodology:

Five-Treatment, 5-period, fasted, balanced crossover study with a three to four day washout between each dose.

Number of Subjects:

Fifteen (15) healthy volunteers.

Diagnosis and Main Criteria for Inclusion:

Healthy male volunteers, aged greater than 18 and less than 40 years, and within ±10% of ideal body weight.

Duration of Treatment:

The test treatment was administered as a single oral dose. In each treatment period the duration of stay in the clinic was approximately 12 hours prior to dosing and 24 hours after dosing. There were 5 treatment periods. There was a 3-4 day washout period between each dose administration (for example, a Monday/Thursday or equivalent dosing schedule).

The total duration of the study was approximately 28 days. Total confinement during the study was 10 days and 10 nights.

During each day of the 28 day period the blood of each of the patients was extracted and the concentration of bicifadine in the blood was evaluated and analyzed and reported in ng/ml.

A sensitive and specific assay was developed and validated for the determination of bicifadine in human plasma. Bicifadine and an internal standard were separated from plasma by solid-liquid extraction and the samples were analyzed by Liquid Chromatography/Mass Spectrometry/Mass Spectrometry (LC/MS/MS) in the APCI positive mode according to well known methods. The assays were carried out using a 0.5 mL sampling volume of human plasma and the validated quantitation limit of the method was 5.0 $ng \cdot mL^{-1}$ of bicifadine. A plasma standard curve was daily elaborated between 5 to 2000 $ng \cdot mL^{-1}$ of bicifadine. A 11×2 weighted quadratic regression analysis was used to determine the b coefficient, intercept and determination coefficient. The calibration lines were plotted on the basis of chromatographic peak area ratios (analyte/internal standard) versus the corresponding plasma concentrations. The concentrations are expressed as ng of bicifadine per millilitre of plasma. Samples collected during the study were assayed in runs composed of a calibration curve and a batch of six quality control samples. The low relative standard deviation and bias calculated during the within-run and between-run assays of the validation demonstrated the fidelity of this method for routine measurement of bicifadine in human plasma samples collected during pharmacokinetic studies.

Heparinized plasma was obtained from non-infectious subjects. Following selectivity testing, as a lack of any interference has been demonstrated, plasma samples were pooled in order to get a sufficient volume of the same matrix to spike calibration standards and quality control samples. A sufficient volume of drug-free heparinized control plasma was prepared for the whole study. Calibration standards were prepared and a plasma standard curve was performed each run of the assay. The daily calibration curves were obtained, throughout the assay, by plotting the chromatographic peak area ratios (compound/internal standard) versus the known concentrations of bicifadine. A $1/X^2$ weighted quadratic regression analysis was used to determine the b coefficient, intercept and determination coefficient. These parameters were used to calculate the concentrations of bicifadine in quality control samples and in the biological samples collected during the study. The plasma calibration curves realized during the analysis of the study samples were straight lines over the studied range of concentrations.

Liquid chromatography was performed using an ALLIANCE system from Waters. The analytical column (50 mm×4.6 mm ID) was packed with an Hypersil BDS C-18 stationary phase. The mobile phase was a mixture of 30% acetonitrile, 35% methanol, 0.5% formic acid filled up to 100% with water. The HPLC was connected to a PE SCIEX API 3000 system operating in the APCI positive mode with the following parameters: Nebulizer gas: Nitrogen (3 bar) Auxiliary gas: Air (4 bar) Curtain gas: Nitrogen (6 bar). The API 3000 MS/MS system was remotely controlled by a PC using NT rev 4.0 US Operating System, and running Applied Biosystem Analyst software rev 1.1. The MS/MS system was focused in the Multiple Reaction Monitoring (MRM) mode to monitor the following ion transitions: −174.2 133.1 for bicifadine; 227.9 187.2 for internal standard.

The concentration of ng/ml of drug in the plasma was plotted against time and various features of the resulting curve were measured and reported in table 6 as follows:

Abbreviations:

Area under the drug plasma concentration versus time curve=$AUC_1$

Area under the drug plasma concentration versus time curve extrapolated to infinity=$AUCO_{inf}$ The maximum measured concentration of the drug in the plasma=Cmax.

The time at which the Cmax was measured=tmax.

Terminal elimination rate=$Lamda_z$

Apparent half life=t1/2.

TABLE 6

Pharmacokinetic Comparison of Bicifadine SR and IR Formulations

| PK Parameters | TrtA-100 mg Bicifadine IR tablet N = 15 | TrtB-200 mg Bicifadine SR (40% Methocel K100M) N = 15 | TrtC-200 mg Bicifadine SR (60% Methocel K100M) N = 15 | TrtD-200 mg Bicifadine SR (40% Methocel K100M and 10% Carbopol) N = 15 | TrtE-200 mg Bicifadine SR (15% Carbopol) N = 15 |
|---|---|---|---|---|---|
| $AUC_{inf}$ (ng/mL · h) | 2621.81 ± 838.33 | 4837.19 ± 1801.19t | 3506.81 ± 1819.09* | 3764.95 ± 1538.40 | 3160.12 ± 2071.62t |
| CV % | 32.0 | 37.2 | 51.9 | 40.9 | 65.6 |
| $AUC_{last}$ (ng/mL · h) | 2578.75 ± 805.08 | 4460.36 ± 1390.56 | 3293.94 ± 1372.03 | 3273.54 ± 995.39 | 3308.39 ± 1573.14 |
| CV % | 31.2 | 31.2 | 41.7 | 30.4 | 47.6 |
| Cmax (ng/mL) | 1485.93 ± 495.32 | 546.36 ± 103.69 | 440.35 ± 81.74 | 545.58 ± 165.75 | 398.82 ± 125.89 |
| CV % | 33.3 | 19.0 | 18.6 | 30.4 | 31.6 |

TABLE 6-continued

Pharmacokinetic Comparison of Bicifadine SR and IR Formulations

| PK Parameters | TrtA-100 mg Bicifadine IR tablet N = 15 | TrtB-200 mg Bicifadine SR (40% Methocel K100M) N = 15 | TrtC-200 mg Bicifadine SR (60% Methocel K100M) N = 15 | TrtD-200 mg Bicifadine SR (40% Methocel K100M and 10% Carbopol) N = 15 | TrtE-200 mg Bicifadine SR (15% Carbopol) N = 15 |
|---|---|---|---|---|---|
| Tmax (h) | 0.53 ± 0.26 | 1.47 ± 0.90 | 1.50 ± 0.93 | 0.80 ± 0.44 | 1.52 ± 0.91 |
| CV % | 47.9 | 61.1 | 61.7 | 55.4 | 59.8 |
| Lambda$_z$ (h$^{-1}$) | 0.41 ± 0.13 | 0.16 ± 0.09† | 0.22 ± 0.13* | 0.11 ± 0.08† | 0.20 ± 0.10† |
| CV % | 31.1 | 54.0 | 61.8 | 73.1 | 51.3 |
| t ½ (h) | 1.84 ± 0.56 | 5.55 ± 2.49† | 4.74 ± 3.38* | 9.36 ± 4.63† | 4.96 ± 3.36† |
| CV % | 30.8 | 44.8 | 71.2 | 49.5 | 67.8 |

*n = 14
†n = 12 ††n = 9

From the plotted plasma profiles for each of the treatments, and the pharmacokinetic parameters reported in the table, the tablets which contained 40% by weight hydroxymethyl cellulose had a higher concentration of drug in the blood stream for longer periods of time than those produced from tablets containing 60% hydroxypropyl methylcellulose slow release polymer matrix. This was clearly observed by comparing Treatment B with Treatment C. In addition, Treatment B which contained 40% by weight of hydroxypropylmethyl cellulose hydrophilic slow release polymer matrix produced superior results with regard to the maintenance of bicifadine in the blood stream for longer periods of time than that produced in Treatment E by the tablets containing either polyacrylic acid alone as the slow release polymer matrix or in a mixture with hydroxypropyl methyl cellulose (Treatment D).

According to these findings, those skilled in the art will readily appreciate that a wide range of alternative SR formulations are operative within the invention, and these formulations can be adjusted to achieve specific pharmacokinetic results that will be desired in different embodiments of the invention, e.g., to optimize the formulations according to such variables as pain type (acute, chronic, or neuropathic), nature of injury/condition being treated, and patient-specific variables such as age, weight, condition, treatment history and response, etc.

Example 15

Preparation of Exemplary 200 mg Bicifadine HCl SR Tablets

Quantitative Composition of Tablet Formulations:

| Product | Bicifadine HCl Tablets 200 mg SR | |
|---|---|---|
| Ingredients | mg/tab | %/tab |
| Bicifadine HCl | 200.00 | 44.44 |
| Hypromellose, USP | 110.00 | 24.44 |
| Bibasic calcium phosphate dihydrate, USP | 135.50 | 30.11 |
| Colloidal silicon dioxide, NF | 2.25 | 0.50 |

-continued

| Product | Bicifadine HCl Tablets 200 mg SR | |
|---|---|---|
| Ingredients | mg/tab | %/tab |
| Magnesium stearate vegetable grade, NF | 2.25 | 0.50 |
| Total | 450.00 | 100.00 |
| Opadry II blue 85F90631 (3% w/w) | 13.5 | 3.00 |
| Purified water, USP* | 54.0 | — |

*Evaporates during coating process

The above table details another exemplary bicifadine HCl SR tablet formulation (hereafter referred to as "formulation M"). In this example, bicifadine HCl is used "as is" and the potency is based on the salt. Hypromellose (hydroxypropylmethylcellulose), acts as a rate controlling hydrophilic polymer for sustained release. Dibasic calcium phosphate dihydrate is a carrier. Colloidal silicon dioxide is a glidant, and magnesium stearate is a lubricant.

The tablets were manufactured using a slugging/roller compaction (chilsonation) process. The process involves blending the bicifadine with a portion of the colloidal silicon dioxide and magnesium stearate and then slugging/roller compacting (chilsonating) and milling the compacted material. It is then blended with the remaining ingredients, compressed and film-coated with a 20% opadry II blue suspension. The resulting tablets have a hardness ranging from about 8 Kp to about 12 Kp.

Example 16

In Vivo Pharmacokinetic Comparison of Sustained Release (SR) and Immediate Release (IR) Bicifadine Formulations The present study provides an in vivo pharmacokinetic comparison for exemplary SR and IR bicifadine formulations, based on plasma concentration time-course analysis following administration of the exemplary bicifadine SR and IR oral tablets to human subjects. The data for IR pharmacokinetics were obtained from a single-dose, balanced, crossover, placebo-controlled, study in healthy adult male subjects administered one 100 mg immediate release (IR) tablet (Formulation A; Example 12).

The data for SR pharmacokinetics were obtained from a randomized, single dose, open-label, two-period, two-sequence, two-treatment crossover bioequivalence study in 24 healthy adult male human subjects administered two exemplary bicifadine 200 mg SR formulations (formulation M from example 15, and a second 200 mg SR tablet, "formulation N"). Formulation N was produced as above, using 110 mg hydroxypropylmethylcellulose, 135.5 mg dibasic calcium phosphate, 2.25 mg colloidal silicon dioxide, 2.25 mg magnesium stearate, 13.5 mg Opadry II blue, and 54 mg purified water USP (evaporates during coating process). Table 7 below provides the comparative pharmacokinetic metrics for the IR formulation and formulation M. FIG. 1, below, graphically depicts the pharmacokinetic metrics for the IR formulation (triangles) in comparison to both SR formulations (diamonds indicate formulation M data, squared indicate formulation N data), which were shown to be essentially bioequivalent).

TABLE 7

Pharmacokinetic Metrics [mean (SD)] for IR and SR Bicifadine Formulations

| Formulation | IR | SR (Formula M) |
|---|---|---|
| Dose | 100 mg | 200 mg |
| $AUC_t$ (ng/mL * h) | 5158* | 4586 |
| $C_{max}$ (ng/mL) | 2972* | 721 |
| $t_{max}$ (h) | 0.53 | 1.63 |
| $t_{1/2}$ (h) | 1.84 | 3.74 |

*Dose-adjusted to 200 mg

Example 17

Analgesic Efficacy and In Vivo Pharmacokinetics of Bicifadine SR Tablets in Acute Dental Pain Studies A two-center, double-blind, placebo-controlled, randomized study of subjects administered an exemplary bicifadine SR formulation (Formulation F; Example 1) in 200 mg, 400 mg (two tablets), and 600 mg (three tablets), or Tramadol 100 mg in the treatment of post-operative dental pain was conducted. Healthy adult male and female human subjects who underwent surgical extraction of two or more impacted third molars were enrolled in the study. Following cessation of the local anesthetic effect and onset of pain of at least 40 mm intensity on the 100 mm VAS, patients were randomized to into 1 of the 5 treatment arms (n~108 per arm) and remained in the clinic for the subsequent 12 hours of the study. The study subjects were randomized to receive either a single dose of: 200 mg, 400 mg or 600 mg bicifadine SR tablets, Tramadol 100 mg, or Placebo. Analgesia ratings were obtained over a 12 h post-dosing period. Rescue medication (acetaminophen) was available, but no analgesia measures were taken after the use of rescue medication by a given patient. A subset of 150 patients provided blood samples at 0.5 hr and hourly intervals following dosing with study medication for the purpose of determining bicifadine levels (n=90). Bicifadine was measured with a validated LC/MS/MS assay that had a lower limit of quantization of 4 ng/mL and a range of 4 to 1652 ng/mL.

The main efficacy endpoints utilized in the overall study (n~540) were the individual assessment of Pain Severity and Pain Relief scores at a given time point; the derived scores (PID, PRID, SPID, SPRID, TOTPAR), and the global improvement. The last observation carried forward (LOCF) approach was used to estimate change over time for those patients who used rescue medication. For the full study efficacy evaluations, one-way analysis of covariance with baseline pain severity as a covariate was applied. The global tests which included all treatment arms were followed by post-hoc comparisons of the individual treatment arms vs. placebo.

Plasma time course profiles were determined in a subset of 30 subjects (15 male/15 female) from each treatment group. These pharmacokinetic results are presented in Table 8.

TABLE 8

Pharmacokinetics [mean (SD)]

| | Dose (mg) | | |
|---|---|---|---|
| | 200 | 400 | 600 |
| $C_{max}$ (ng/mL) | 572 (248) | 1284 (594) | 1908 (476) |
| $t_{max}$ (h) | 2.90 (1.56) | 3.55 (1.91) | 3.77 (1.55) |
| $AUC_\infty$ (ng/mL * h) | 4292 (2286) | 9027 (4740) | 14167 (5711) |
| $t_{1/2}$ (h) | 4.44 (1.44) | 4.07 (1.55) | 3.57 (1.06) |

Pharmacokinetic linearity of peak and total exposure was apparent across the single dose range of 200 to 600 mg. Times to peak exposure ($t_{max}$=2.90 to 3.77 h) were slightly longer than in previous studies, where observed $t_{max}$ values for a bicifadine SR formulation ranged between 1.0-2.3 hours, although apparent terminal half-lives were similar. This delay of $t_{max}$ appears to relate to the effects of dental surgery, possibly due to delayed gastric emptying, as a similar post-surgery $t_{max}$ delay has been reported in ibuprofen-treated dental surgery patients (F. Jamali, C. Kunz-Dober, *Pain-mediated altered absorption and metabolism of ibuprofen: An explanation for decreased serum enantiomer concentration after dental surgery*, Br. J. Clin. Pharmacol. 47:391-396, 1999). Pain severity ratings at $t_{max}$ correlated significantly with $C_{max}$. Subjects with $C_{max}$>1000 ng/mL had a significantly higher odds ratio of having a lower pain severity rating at t, total No differences in peak ($C_{max}$) or total (AUC) exposure were observed between genders.

Figure 2:
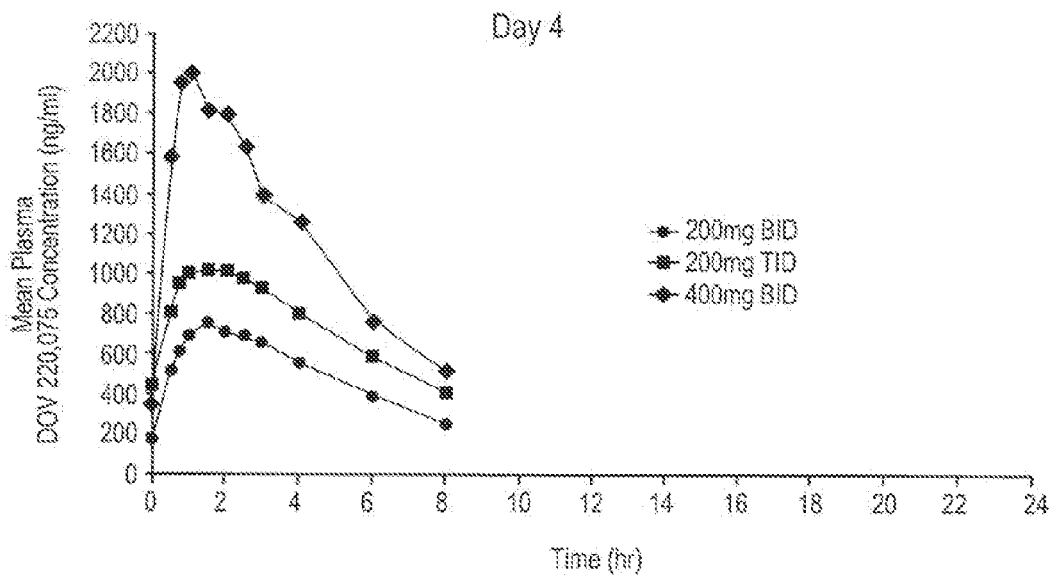
FIG. 2 illustrates mean plasma concentration time course data following administration of 200 mg BID, 200 mg TID, and 400 mg BID (multiple dose, steady-state profiles) of an exemplary bicifadine SR formulation according to the invention administered to subjects in an acute dental pain clinical trial.

FIG. 2 graphically depicts mean plasma concentration time course data on Day 4 following administration of 200 mg BID, 200 mg TID, and 400 mg BID (multiple dose, steady-state profiles within a dosing interval at steady state) in this acute dental pain study.

Figure 3:
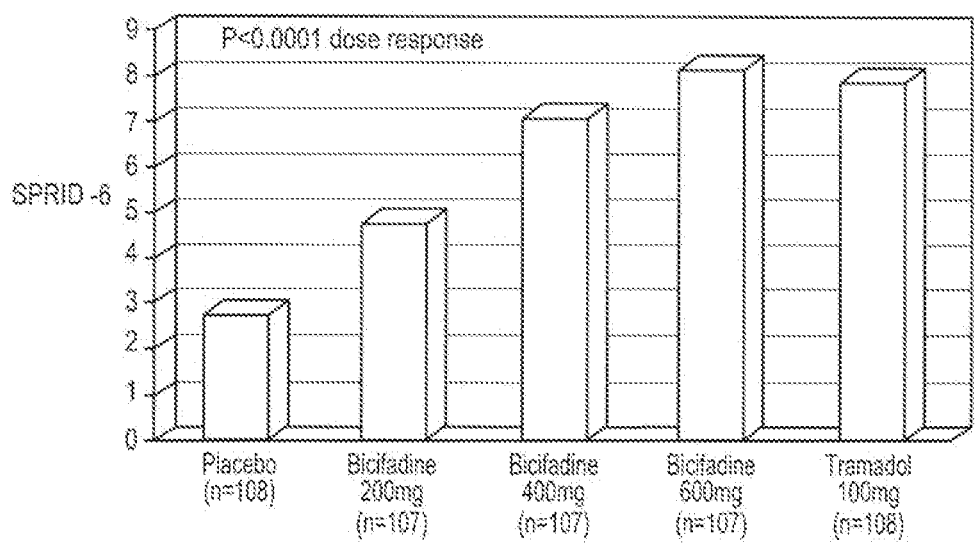
FIG. 3 illustrates the dose-response relationship for analgesic effects of bicifadine and tramadol relative to placebo in an acute dental pain study.

FIG. 3 illustrates the dose-response relationship for analgesic effects of bicifadine and tramadol relative to placebo in this acute dental pain study.

The results of this study demonstrate a clear, statistically significant (P<0.001) dose-response relation for SPRID-6 and other derived analgesia scores in patients with pain following third molar surgery. The magnitude of the effects at 400 mg and 600 mg of bicifadine were numerically comparable to that of 100 mg tramadol and were statistically superior to placebo. Bicifadine at 200 mg was better than placebo on some measures, but on all analgesia measures the effects were lower than that of 400 mg or 600 mg, and, as such 200 mg represented a minimally effective dose in this study.

The relationship between mean pain relief ratings (PRR) and mean plasma bicifadine levels was determined at three exemplary plasma level ranges: between 0-500 ng/ml, 500-1000 ng/ml, and >1000 ng/ml, respectively. A clear positive relationship was observed across 3 ranges of bicifadine levels. In particular, bicifadine plasma concentrations in the >1000 ng/ml range were associated with a PR score approximately 3 times as high as plasma concentrations in the 0-500 ng/ml range (p<0.001, Hierarchical Linear Model analysis).

The probability of treatment response as a function of bicifadine blood concentration levels was also determined. Association between the probability of treatment response and bicifadine blood concentration levels was investigated with the widely known Generalized Estimating Equation (GEE) approach. For the purpose of the GEE analyses described here, bicifadine blood concentration was treated as a continuous independent (predictor) variable. Treatment (analgesic) response served as a dichotomous (yes, no) dependent variable in the GEE model. In particular, treatment response for each individual patient for each of the time points was defined as a Pain Relief Rating of 3 or more (range 0-4). Results of the GEE analyses indicated that the association between bicifadine plasma levels and the likelihood of treatment response reached significance (p=0.006; Odds Ratio of Response for an increase of 500 ng/ml in bicifadine blood levels was 1.59).

In the pharmacokinetic portion of this study that employed 90 patients, there was a clear dose proportional relationship between bicifadine dose and AUC, a relationship demonstrated in prior pharmacokinetic studies conducted in smaller numbers of normal volunteers.

The foregoing studies demonstrate a positive dose-dependent relationship for both the pharmacokinetics (AUC, Cmax) of bicifadine and the pharmacodynamic measures of efficacy for treating acute dental pain. Plasma bicifadine levels>1000 ng/ml were associated with the greatest pain relief. Drug levels between 500-1000 ng/ml were associated with significant analgesic efficacy. Lower plasma drug levels of 500 ng/ml or less were not associated with significant analgesic effects in this acute dental pain study. In respect to analyses performed on individual patients identified as responders or nonresponders to bicifadine, these distinct categories of subjects also showed a significant relationship with plasma drug levels, with responders exhibiting significantly higher blood levels of bicifadine than nonresponders.

Example 18

Comparative Side Effect Profiles of Sustained Release and Immediate Release Bicifadine Formulations A side-by side comparison of side effect profiles of sustained release SR bicifadine formulations (side effect data from studies using SR formulations F and M from examples 1 and 15 were pooled) and an exemplary immediate release (IR) bicifadine formulation (Formulation A; example 12) was conducted. These comparisons were performed using 5 bicifadine dose levels (0-149 mg/day, 150-399 mg/day, 400-599 mg/day, 600-799 mg/day and >=800 mg/day) on 7 parameters (Euphoria, Dizziness, Headache, Mydriasis, Nausea, Sleepiness/Drowsiness, and Vomiting) using the Fisher exact test, according to generally known methods.

The results of the IR vs SR comparisons for different dose ranges of bicifadine are shown in Table 9 below.

TABLE 9

Side Effect Profiles of Bicifadine SR and IR Formulations

| Event | Dosage Form | Placebo | 400-599 mg | 600-799 mg | ≥800 mg |
|---|---|---|---|---|---|
| Euphoria | IR | | (80.0%) | (63.6%) | (90.0%) |
| | SR | (0.0%) | (1.3%) | (4.6%) | (2.0%) |
| | p-Value | 0.217 | <0.001 | | <0.001 |
| Dizziness | IR | (0.0%) | (60.0%) | (60.0%) | (70.0%) |
| | SR | (7.3%) | (1.3%) | (11.7%) | (7.0%) |
| | p-Value | <0.001 | <0.001 | 0.0119 | <0.001 |
| Sleepiness/ | IR | (0.0%) | (80.0%) | (9.1%) | (10.0%) |
| Drowsiness | SR | (5.3%) | (4.2%) | (10.7%) | (3.3%) |
| | p-Value | <0.001 | <0.001 | 1.0000 | 0.3075 |
| Nausea | IR | (0.0%) | (20.0%) | (18.2%) | (80.0%) |
| | SR | (14.9%) | (24.7%) | (32.5%) | (10.2%) |
| | p-Value | <0.001 | 1.0000 | 0.5119 | <0.001 |
| Mydriasis | IR | (0.0%) | (90.0%) | (30.0%) | (100%) |
| | SR | (0.3%) | (4.9%) | (11.8%) | (0.4%) |
| | p-Value | 1.0000 | <0.001 | 0.1142 | <0.001 |
| Headache | IR | (0.0%) | (20.0%) | (27.3%) | |
| | SR | (8.5%) | (10.9%) | (13.2%) | |
| | p-Value | <0.001 | 0.3082 | 0.1810 | |

The data presented in Table 9 clearly demonstrate that for similar daily doses of bicifadine SR and IR formulations, there is a marked and unexpected decrease in the occurrence of specific adverse events elicited by the SR formulation in comparison to the IR formulation.

Example 19

Therapeutic Efficacy of a Reduced Bicifadine Dosing Regimen to Treat Chronic Pain The present study evaluated the therapeutic efficacy of a reduced dosing regimen employing bicifadine in a bi-daily (BID) dosing protocol to treat chronic low back pain (CLBP). More than 800 study subjects were recruited in this study, and a subset of these subjects was administered 400 mg of a sustained release oral dosage form (formula M; example 15) of bicifadine BID to evaluate the long-term analgesic efficacy of bicifadine for treating CLBP. As an efficacy comparator for these studies, a second subset of the study subjects was treated according to the standard of care (SOC) for CLBP treatment, which provided a concurrent control for efficacy as well as spontaneous occurrence of serious adverse events. The following outcome measures were assessed in the study:
1. Pain Severity Rating (VAS);
2. SF-McGill Pain Questionnaire (SF-MPQ);
3. Roland-Morris Disability Rating;
4. Short-Form 36 (SF-36) Health Survey
5. Incidence of Discontinuation due to lack of efficacy; and
6. Time to Discontinuation due to lack of efficacy.

Inclusion criteria for study subjects, as selected for other studies herein, included the following: Subjects were at least 18 years of age. If subject was female and of childbearing potential, the subject had to have a negative serum pregnancy test during the screening period. Subjects were required to have drug and alcohol toxicology screening results during the screening period. Subjects exhibited lower back pain that was either localized to the lower back, or radiating into the lower extremity (assessed as Class 1, Class 2, or Class 3 according to the widely known and practiced, Quebec Task Force Classification for Spinal Disorders. Quebec Classes 4, 5 and 8 were exclusionary, i.e., study subjects were without detectable weakness by neurological examination, and without spinal instability or acute fracture. Subjects had on average required daily analgesic medication for low back pain for at least 3 months immediately prior to the screening period, and had a score of at least 10 on the 24-point Roland-Morris Disability Questionnaire, and a Pain Severity Rating (PSR) of at least 40 mm on a 100 mm Visual Analog Scale (VAS), at the baseline visit.

Other exclusionary criteria in this study included: Low back pain due to acute fracture, infection, severe osteoporosis, malignancy, marked scoliosis, or severe congenital malformation such as spina bifida; Receipt of an epidural injection of corticosteroid in the lower back within 1 month prior to the baseline visit; Use of any antidepressant for pain or sleep (including SSRIs or SNRIs), anti-epileptic, or muscle relaxant, or receipt of transcutaneous electrical nerve stimulation, chiropractic adjustment, or acupuncture within 3 weeks prior to the baseline visit; Use of any antidepressant (including SSRIs or SNRIs) for depression within 3 months prior to the baseline visit; Use of any opioid analgesic or benzodiazepine (or other sedative-hypnotic) within 2 weeks prior to the baseline visit; Use of any NSAID (except aspirin<81 mg per day or <325 mg every other day for cardiac prophylaxis and except ibuprofen) or any non-opioid analgesic (except acetaminophen) within 1 week, or acetaminophen or ibuprofen within 60 hours, prior to the baseline visit; Active malignancy of any type or history of a malignancy within 5 years prior to the first dose of study medication (patients with treated localized basal or squamous cell carcinoma of the skin within 5 years are permitted); Active GI disease (including any GI surgery that, in the Investigator's opinion, would interfere with the absorption of the study medication), or a chronic or acute renal or hepatic disorder; Mental instability, known substance abuse, history of clinically significant depression or alcoholism, or incapacity of being compliant with the requirements of the study; Any clinically significant cardiovascular, renal, endocrine, hepatic, immunologic, respiratory, neurologic, gastrointestinal, psychiatric, or hematologic disease, or any underlying serious medical condition that would preclude patient's participation in the study; and, other standard, relevant exclusion criteria.

Patients who qualified for enrollment into the study completed the PSR test, Roland-Morris Disability Questionnaire, Short Form McGill Pain Questionnaire (SF-MPQ) and the SF-36 quality of life survey at the baseline visit and at various time points throughout the study.

Study subjects were randomized on a 25:6 basis to receive either bicifadine 400 mg BID or SOC treatment, respectively. SOC treatment was provided as any appropriate pharmacological analgesic treatment selected by the investigator based on the subjects' baseline and ongoing presentation. Subjects were permitted to reduce the dose for tolerability reasons, first to bicifadine 300 mg BID, and then, if necessary, to bicifadine 200 mg BID.

Summary statistics, including observed means and standard deviations along with mean change from baseline were summarized by visit for each outcome measure. Incidence of discontinuation due to lack of efficacy and its 95% confidence interval were likewise calculated. The median and its 95% confidence interval and a Kaplan-Meier plot were provided for Time to Discontinuation due to lack of efficacy and other reasons. In addition, analyses for the mean change from baseline at each visit were carried out using paired t-test. All statistical comparisons were made at a comparison-wise error rate of 0.05% (two-sided).

Figure 4:
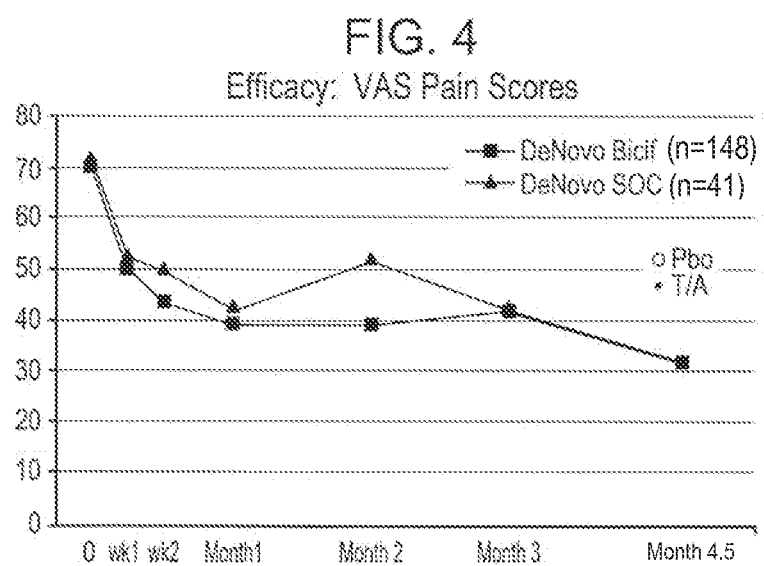
FIG. 4 presents Pain Severity Rating (PSR) data based on a 100 mm visual analogue scale (VAS) developed from long-term clinical studies using bi-daily dosing of bicifadine to treat chronic lower back pain (CLBP).

FIG. 4 presents the VAS pain score results from the foregoing CLBP studies. These data show that bicifadine is surprisingly effective in a reduced, bi-daily (BID) dosing regimen to achieve sustained relief of chronic pain exemplified by CLBP. The therapeutic efficacy of BID-dosed bicifadine in these CLBP clinical studies as determined from pain relief data was comparable to that of standard of care (SOC) treatment over the 4.5 month period of the study. In addition, the therapeutic efficacy of BID-dosed bicifadine in these CLBP clinical studies was demonstrated on the basis of improved functional/activity results, which were also comparable to those observed among SOC-treated subjects in the study.

Example 20

Therapeutic Efficacy of Bicifadine for Treating Functional Disabilities in Human Subjects Associated with Pain The present study evaluated the therapeutic efficacy of bicifadine to treat and/or reduce disability and enhance functional and activity performance in human subjects presenting with pain-associated disability. The study followed the foregoing study design described in Example 19 involving administration of bicifadine to patients presenting with Chronic Low Back Pain (CLBP). In the instant example, the efficacy of bicifadine to treat disability and enhance functional and activity performance in these bicifadine-treated CLBP subjects was particularly pronounced in a subset of patients presenting with more severe disability associated with their CLBP.

In a more highly disabled, poorly functional cohort of patients, characterized by having an initial Roland-Morris Disability Questionnaire (RDQ) score of greater than 17, the effects of bicifadine for reversing disabilities and enhancing functional/activity performance in treated subjects compared to placebo-treated subjects were significant and substantial.

Figure 5:
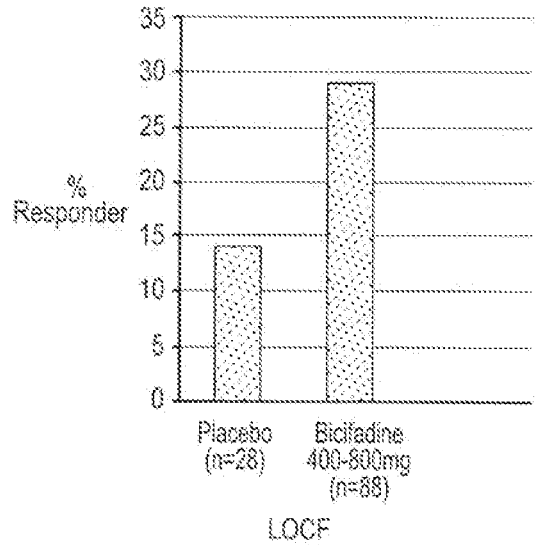
FIG. 5 demonstrates that bicifadine significantly treats pain-associated disability, by enhancing function/activity performance, in Chronic Low Back Pain (CLBP) subjects. In a poorly functional cohort of patients having a baseline Roland-Morris Disability Questionnaire (RDQ) score of greater than 17, bicifadine showed significant activity for reversing disabilities and enhancing functional/activity performance in treated subjects compared to placebo-treated subjects (LOCF="last observation carried forward" calculation method).

As shown in FIG. 5, for patients with moderate to severe impairment at baseline (i.e., subjects presenting with an RDQ>17 at baseline), receiving 400-800 mg/day (i.e., 200, 300 or 400 mg twice daily) disability scores on the RDQ were significantly decreased compared to similarly qualified, placebo-treated subjects. As the data are presented in FIG. 5, patients in the bicifadine-treated and placebo-treated populations were identified as "responders" if their RDQ score showed a 50% or greater improvement from baseline (e.g., a reduction in RDQ from a baseline of 18, to a last observed datum of 9). In the placebo-treated subjects, less than 15% of the patients were classified as "responders", whereas roughly twice this percentage of bicifadine-treated subjects exhibited a 50% or greater reduction in RDQ scores compared to baseline.

Additional analyses identified another major subgroup of patients (in addition to the moderate to severely impaired subgroup noted above) in which the effectiveness of bicifadine was substantial—patients with chronic low back pain along with pain radiating down the leg (sciatica). Patients with low back pain who also had pain radiating down the leg showed a placebo pain response rate that was approximately half of that in patients with low back pain alone. Patients with low back pain and radiating pain were two times more responsive to treatment with bicifadine than patients with only localized back pain and showed an 11 mm improvement in VAS pain score compared to placebo.

The efficacy of bicifadine for reducing pain-related disability and enhancing functionality in CLBP subjects illustrates a separate and distinct therapeutic indication for this drug. Patients with moderate to severe disability due to their back pain (e.g. limited ability to walk up stairs, bend over, lift objects, etc.) had only about one third of the placebo response of patients with mild to moderate disability. The patients with moderate to severe disability also were substantially more responsive to treatment with bicifadine, as described above.

Figure 6:
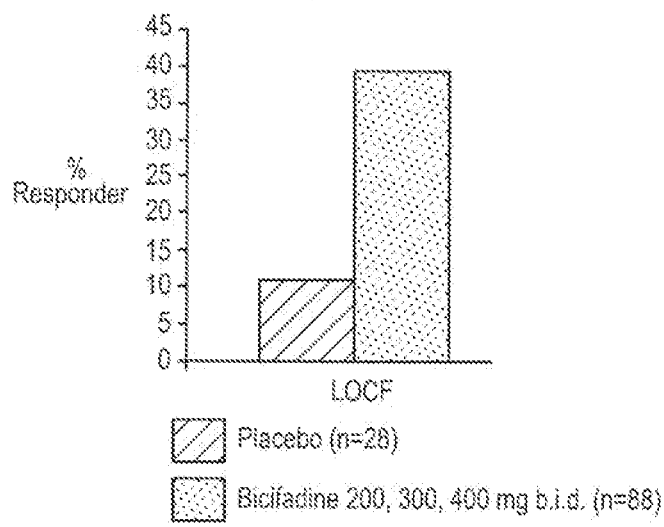
FIG. 6 demonstrates that pain-relief results for bicifadine are also significant and substantial among a moderate to severely disabled cohort of CLBP patients. VAS pain scores in moderate to severely disabled CLBP patients (presenting with a baseline RDQ score greater than 17) were reduced by 50% or more in at least three times as many bicifadine-treated as placebo-treated patients.

Although the disability-reversing and function-enhancing effects of bicifadine are distinct from pain-relief results for the drug, these pain relief results were also substantial and significant for the moderate to severely disabled cohort of CLBP patients. As shown in FIG. 6, the VAS pain scores in moderate to severely disabled CLBP patients (presenting with a baseline RDQ score greater than 17) were also significantly reduced by bicifadine treatment compared to placebo. In fact, the percentage of bicifadine-treated subjects in the moderate to severely disabled cohort that showed at least a 50% reduction in VAS scores was roughly three times the percentage of placebo-treated subjects in the moderate to severely disabled cohort that reported this level of reduction in VAS scores (FIG. 6).

Although the foregoing invention has been described in detail by way of example for purposes of clarity of understanding, persons of ordinary skill in the art will understand that certain changes and modifications may be practiced within the scope of the appended claims which are presented by way of illustration not limitation. In this context, the invention is not limited to the particular formulations, processes, and materials disclosed herein, as such formulations, process steps, and materials may vary somewhat. Also, the terminology employed herein is used for describing particular embodiments only, and is not intended to be limiting of the invention embodied in the claims. Various publications and other reference information have been cited within the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

The disclosures of U.S. patent application No. 10/621,435, filed Jul. 17, 2003, and U.S. Provisional Application No. 60/399,852, filed Jul. 31, 2002, are incorporated herein by reference.

What is claimed is:

1. A method for treating a disability or reducing a functional impairment in a mammalian subject associated with acute pain, chronic pain, or a neuropathic disorder, comprising administering to the mammalian subject in need thereof a therapeutically effective amount of a compound of Formula I

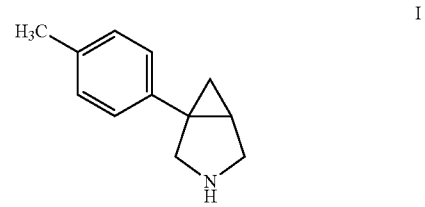

or a pharmaceutically acceptable salt thereof.

2. The method of claim 1, wherein the disability or functional impairment is associated with chronic pain.

3. The method of claim 2, wherein the chronic pain is selected from the group consisting of osteoarthritis pain, rheumatoid arthritis pain, cancer pain, chronic low back pain, chronic lumbar and cervical pain, chronic fibromyalgia pain, chronic pain from arteriovenous malformation, arachnoiditis, chronic pain from root avulsion, chronic postthoracotomy pain, and chronic postmastectomy pain of non-neuropathic origin.

4. The method of claim 3, wherein the chronic pain is chronic low back pain (CLBP).

5. The method of claim 1, wherein the compound of Formula I or a pharmaceutically acceptable salt thereof is formulated with a sustained release vehicle, matrix, binder, or coating material.

6. The method of claim 5, wherein the sustained release vehicle, matrix, binder, or coating material comprises a sustained release polymer.

7. The method of claim 6, wherein the sustained release polymer is selected from the group consisting of consisting of ethylcellulose, hydroxyethyl cellulose, hydroxyethylmethyl cellulose, hydroxypropyl cellulose, hydroxypropylmethyl cellulose, hydroxypropylmethyl cellulose phthalate, hydroxypropylmethylcellulose acetate succinate, hydroxypropylmethylcellulose acetate phthalate, sodium carboxymethylcellulose, cellulose acetate phthalate, cellulose acetate trimellitate, polyoxyethylene stearates, polyvinyl pyrrolidone, polyvinyl alcohol, copolymers of polyvinyl pyrrolidone and polyvinyl alcohol, polymethacrylate copolymers, and mixtures thereof.

8. The method of claim 7, wherein the sustained release polymer is hydroxypropylmethyl cellulose.

9. The method of claim 1, wherein the disability or functional impairment is associated with acute pain.

10. The method of claim 9, wherein the acute pain results from a burn; cut; wound; trauma; surgery; headache; sprain; bone fracture; fibromyalgia;

acute lower back pain; dorsopathy; dysmenorrhea; infection; dysfunction of the liver, pancreas, endocrine glands, kidney, bladder, gall bladder, spleen, hematopoietic system, vasculature or other body organ or tissue; torn or injured muscle, ligament, or tendon; or acute exacerbation of a chronic or intermittent pain condition.

11. The method of claim 1, wherein the disability or functional impairment is associated with a neuropathic disorder.

12. The method of claim 11, wherein the neuropathic disorder is selected from the group consisting of diabetic neuropathy, peripheral neuropathy, distal symmetrical polyneuropathy, post-herpetic neuralgia, trigeminal neuralgia, alcoholism-related neuropathy, HIV sensory neuropathy, sciatica, spinal cord injury, post-stroke neuropathy, multiple sclerosis, Parkinson's disease, idiopathic or post-traumatic neuropathy, mononeuritis, cancer-associated neuropathy, peripheral nerve trauma, nerve transection, carpal tunnel injury, neuropathy associated with Fabry's disease, vasculitic neuropathy, neuropathy associated with Guillain-Barre syndrome, entrapment neuropathy, and phantom limb syndrome.

13. The method of claim 11, wherein the neuropathic disorder is associated with fibromyalgia, Wallenberg's syndrome, connective tissue disease, plexus irradiation, ischemic irradiation, hematomyelia, dysraphism, tumor compression, arteriovenous malformation, syphilitic myelitis, commissural myelotomy, arachnoiditis, root avulsion, chronic lower back pain syndromes of neuropathic origin, or reflex sympathetic dystrophy.

14. The method of claim 1 comprising administering a therapeutically effective amount of 1-(4-methylphenyl)-3-azabicyclo[3.1.0]hexane hydrochloride.

15. The method of claim 1 comprising administering a therapeutically effective amount of (+)-1-(4-methylphenyl)-3-azabicyclo[3.1.0]hexane or a pharmaceutically acceptable salt thereof.

16. The method of claim 1 comprising administering a therapeutically effective amount of (+)-1-(4-methylphenyl)-3-azabicyclo[3.1.0]hexane or a pharmaceutically acceptable salt thereof substantially free of (+1-(4-methylphenyl)-3-azabicyclo[3.1.0]hexane or a pharmaceutically acceptable salt thereof.

17. The method of claim 1 comprising administering a therapeutically effective amount of (−)-1-(4-methylphenyl)-3-azabicyclo[3.1.0]hexane or a pharmaceutically acceptable salt thereof.

18. The method of claim 1 comprising administering a therapeutically effective amount of (−)-1-(4-methylphenyl)-3-azabicyclo[3.1.0]hexane or a pharmaceutically acceptable salt thereof substantially free of (+)-1-(4-methylphenyl)-3-azabicyclo[3.1.0]hexane or a pharmaceutically acceptable salt thereof.

19. The method of claim 1 comprising administering a therapeutically effective amount of polymorph form B of 1-(4-methylphenyl)-3-azabicyclo[3.1.0]hexane hydrochloride.

20. The method of claim 1 comprising administering a therapeutically effective amount of polymorph form B of 1-(4-methylphenyl)-3-azabicyclo[3.1.0]hexane hydrochloride substantially free of polymorph form A of 1-(4-methylphenyl)-3-azabicyclo[3.1.0]hexane hydrochloride.

21. The method of claim 1 comprising administering a therapeutically effective amount of polymorph form A of 1-(4-methylphenyl)-3-azabicyclo[3.1.0]hexane hydrochloride.

22. The method of claim 1 comprising administering a therapeutically effective amount of polymorph form A of 1-(4-methylphenyl)-3-azabicyclo[3.1.0]hexane hydrochloride substantially free of polymorph form B of 1-(4-methylphenyl)-3-azabicyclo[3.1.0]hexane hydrochloride.

23. The method of claim 1 comprising administering about 25 to 1200 mg of the compound of Formula I or a pharmaceutically acceptable salt thereof.

24. The method of claim 1 comprising administering about 50 to 1000 mg of the compound of Formula I or a pharmaceutically acceptable salt thereof.

25. The method of claim 1 comprising administering about 75 to 800 mg of the compound of Formula I or a pharmaceutically acceptable salt thereo.

26. The method of claim 1 comprising administering about 100 to 600 mg of the compound of Formula I or a pharmaceutically acceptable salt thereof.

27. The method of claim 1 comprising administering about 100 to 400 mg of the compound of Formula I or a pharmaceutically acceptable salt thereof.

28. The method of claim 1 comprising administering about 100 to 200 mg of the compound of Formula I or a pharmaceutically acceptable salt thereof.

* * * * *